US006723342B1

(12) United States Patent
Augello et al.

(10) Patent No.: US 6,723,342 B1
(45) Date of Patent: *Apr. 20, 2004

(54) EDIBLE COATING COMPOSITION

(75) Inventors: Michael Augello, Marlboro, NJ (US);
Sheila M. Dell, New Hope, PA (US);
Domingo C. Tuason, Bensalem, PA (US); James J. Modliszewski, Brick, NJ (US); Thomas A. Ruszkay, Hockessin, DE (US); David E. Werner, West Grove, PA (US)

(73) Assignee: FMC Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/632,228

(22) Filed: Aug. 4, 2000

Related U.S. Application Data

(63) Continuation-in-part of application No. 09/491,724, filed on Jan. 27, 2000, now Pat. No. 6,432,448.
(60) Provisional application No. 60/172,526, filed on Dec. 17, 1999, provisional application No. 60/167,407, filed on Nov. 24, 1999, provisional application No. 60/162,514, filed on Oct. 29, 1999, provisional application No. 60/133,092, filed on May 7, 1999, and provisional application No. 60/119,005, filed on Feb. 8, 1999.

(51) Int. Cl.$^7$ ................................................. A61K 9/36
(52) U.S. Cl. .................... 424/479; 424/474; 424/475; 424/476; 424/463; 424/480; 424/482; 424/490; 106/162.9; 106/162.8
(58) Field of Search .................. 424/475, 479, 424/482, 490, 463, 474, 476, 480; 106/162.9, 162.8

(56) References Cited

U.S. PATENT DOCUMENTS 2,134,714 A 11/1938 Glassman
2,881,085 A 4/1959 Endicott et al.

(List continued on next page.)

FOREIGN PATENT DOCUMENTS

| DE | 25 22 483 | 12/1975 |
|---|---|---|
| DE | 2820981 | 4/1979 |
| DE | 37 20 757 | 1/1989 |
| DE | 38 29 942 | 3/1989 |
| DE | 39 29 184 | 3/1991 |

(List continued on next page.)

OTHER PUBLICATIONS

Chemical Abstracts, vol. 100, No. 23, Jun. 4, 1984 abstract 100: 190544j.
Chemical Abstracts, vol. 101, No. 11, Sep. 10, 1984 abstract 101: 89243f.
Chemical Abstracts, vol. 101, No. 17, Oct. 22, 1984 abstract 101: 150241x.
Rowe, "Some Fundamental Properties Of Polymeric Materials And Their Application In Film Coating Formulations" Int. J. Pharm. Tech & Prod. Mfr., (3) 1982.
Rowe & Forse, "The Effect Of Polymer Molecular Weight On The Incidence Of Cracking And Splitting On Film Coated Tablets", Communications, J. Pharm. Pharmacol, 1980, 32:583.
Translation of JP 51–123815 1978.
Translation of JP 49–133515 1974.
Okhamafe A. et al, J. Pharm. Pharmacol. 37: 449–454, 1985 "Stress Crack Resistance . . . Tablet Film Coating Systems".
Okhamafe A. et al, J. Pharm. Pharmacol. 41: 1–6, 1989 "Thermal Characterization . . . Film Coating Formulation".
Translation of WO 99/07347 Feb. 18, 1999.
International Search Report and Written Opinion for PCT/US00/29848 May 4, 2000.
Leon Lachman, Herbert Lieberman & Joseph Kanig, The Theory and Practice of Industrial Pharmacy, 3rd ed. (Philadelphia, PA.: Lea & Febiger, 1986),pp. 76–77,321,327–328.
Kirk–Othmer Encyclopedia of Chemical Technology; vol. 4, pp. 653–661, John Wiley & Sons, Inc. (1964).
Supplementary European Search Report for Application No. EP 00 90 7193.
The Use of Carrageenan in Mixture with Microcrystalline Cellulose and its Functionality for Making Tablets., Katharina M. Picker, European Journal of Pharmaceutics and Biopharmaceutics.,48(1), pp. 27–36 (1999).
WO/US00/21397 Search Report dated Nov. 20, 2000.
"A clear advance in convential coatings," Introducing Lustre Clear™ Microcrystalline Cellulose/Carrageenan–Based Coating System brochure, FMC BioPolymer, 1999, 17 pages.
Colliopoulos, J.A., et al., "Rheological properties of microcrystalline cellulose (MCC) carrageenan aqueous film coating," Annual Meeting, Nov. 14–18, 1999, AAPS Abstract No. 3480, 1 page.
Dell, S.M., et al., "Evaluation of mechanical properties of free films of aqueous coating systems," Annual Meeting, Nov. 14–18, 1999, AAPS Abstract No. 2906, 1 page.
Dell, S.M., et al., "Evaluation of microcrystalline cellulous (MCC): carrageenan mixture as a film former in conventional aqueous film coating," Annual Meeting, Nov. 14–18, 1999, AAPS Abstract No. 2925, 1 page.

(List continued on next page.)

Primary Examiner—James M. Spear
Assistant Examiner—Liliana Di Nola-Baron
(74) Attorney, Agent, or Firm—Woodcock Washburn LLP

(57) ABSTRACT

An edible, hardenable coating composition containing microcrystalline cellulose and carrageenan and at least one of a strengthening polymer, a plasticizer, a surface active agent or a combination thereof. The coating composition of the present invention may be applied to pharmaceutical and veterinary solid dosage forms, confectionery, seeds, animal feed, fertilizers, pesticide tablets, and foods and provides an elegant prompt release coating which does not retard the release of active ingredients from the coated substrate.

29 Claims, No Drawings

U.S. PATENT DOCUMENTS

| | | |
|---|---|---|
| 3,149,039 A | 9/1964 | Jeffries |
| 3,149,040 A | 9/1964 | Jeffries |
| 3,251,824 A | 5/1966 | Battista |
| 3,297,535 A | 1/1967 | Butler et al. |
| 3,407,157 A | 10/1968 | Carstensen et al. |
| 3,438,797 A | 4/1969 | Biddle |
| 3,503,769 A | 3/1970 | McDowell |
| 3,539,365 A | 11/1970 | Durand et al. |
| 3,576,663 A | 4/1971 | Signorino et al. |
| 3,649,302 A | 3/1972 | Daggy |
| 3,751,277 A | 8/1973 | Small et al. |
| 3,835,221 A | 9/1974 | Fulberth et al. |
| 3,851,574 A | 12/1974 | Katz et al. |
| 3,860,733 A | 1/1975 | Morse et al. |
| 3,873,694 A | 3/1975 | Kanig |
| 3,883,458 A | 5/1975 | Mueller et al. ........ 260/26.5 R |
| 3,906,086 A | 9/1975 | Guy et al. |
| 3,906,088 A | 9/1975 | Trichot |
| 3,935,326 A | 1/1976 | Groppenbacher et al. |
| 3,937,966 A | 2/1976 | Godel et al. |
| 3,981,984 A | 9/1976 | Signorino |
| 4,009,131 A | 2/1977 | Farone |
| 4,015,999 A | 4/1977 | Robertson et al. |
| 4,060,598 A | 11/1977 | Groppenbacher et al. |
| 4,095,992 A | 6/1978 | Rudolph et al. |
| 4,112,215 A | 9/1978 | Boessler et al. |
| 4,143,163 A | 3/1979 | Hutchison et al. |
| 4,250,195 A | 2/1981 | Cherukuri et al. |
| 4,252,786 A | 2/1981 | Weiss et al. |
| 4,257,816 A | 3/1981 | Yin et al. |
| 4,263,334 A | 4/1981 | McGinley |
| 4,274,830 A | 6/1981 | Woznicki et al. |
| 4,287,221 A | 9/1981 | Tonedachi et al. |
| 4,292,299 A | 9/1981 | Suzuki et al. |
| 4,295,851 A | 10/1981 | Neumann et al. |
| 4,302,440 A | 11/1981 | John et al. |
| 4,307,117 A * | 12/1981 | Leshik ........ 426/96 |
| 4,311,717 A | 1/1982 | McGinley |
| 4,316,884 A | 2/1982 | Alam et al. |
| 4,324,554 A | 4/1982 | Racciato |
| 4,330,338 A | 5/1982 | Banker |
| 4,336,244 A | 6/1982 | Woznicki et al. |
| 4,340,582 A | 7/1982 | Kriesel et al. |
| 4,341,563 A | 7/1982 | Kurihara et al. ........ 106/171 |
| 4,375,468 A | 3/1983 | Dunn |
| 4,421,738 A | 12/1983 | Yamagiwa et al. |
| 4,432,966 A | 2/1984 | Zeitoun et al. |
| 4,475,919 A | 10/1984 | Woznicki et al. |
| 4,505,890 A | 3/1985 | Jain et al. |
| 4,513,019 A | 4/1985 | Brancq et al. |
| 4,514,384 A | 4/1985 | Gallina |
| 4,524,060 A | 6/1985 | Mughal et al. |
| 4,533,562 A | 8/1985 | Ikegami et al. |
| 4,543,370 A | 9/1985 | Porter et al. |
| 4,556,552 A | 12/1985 | Porter et al. |
| 4,576,646 A | 3/1986 | Branco et al. |
| 4,596,602 A | 6/1986 | Bennett |
| 4,636,261 A | 1/1987 | Heinze |
| 4,643,894 A | 2/1987 | Porter et al. |
| 4,645,662 A | 2/1987 | Nakashima et al. ........ 424/52 |
| 4,652,313 A | 3/1987 | Den Boer et al. |
| 4,661,162 A | 4/1987 | Kurihara et al. |
| 4,665,648 A | 5/1987 | Branco et al. |
| 4,666,703 A | 5/1987 | Kopf |
| 4,683,256 A | 7/1987 | Porter et al. |
| 4,693,750 A | 9/1987 | Bauer et al. |
| 4,693,751 A | 9/1987 | Den Boer et al. |
| 4,704,295 A | 11/1987 | Porter et al. |
| 4,720,378 A | 1/1988 | Forse et al. |
| 4,725,441 A | 2/1988 | Porter et al. |
| 4,750,938 A | 6/1988 | Cottrell |
| 4,784,858 A | 11/1988 | Ventouras ........ 424/468 |
| 4,786,511 A | 11/1988 | Huzinec et al. |
| 4,790,881 A | 12/1988 | Wittwer et al. |
| 4,792,452 A | 12/1988 | Howard et al. |
| 4,802,924 A | 2/1989 | Woznicki et al. |
| 4,814,181 A | 3/1989 | Jordan et al. |
| 4,816,298 A | 3/1989 | Alderman et al. |
| 4,828,841 A | 5/1989 | Porter et al. |
| 4,857,337 A | 8/1989 | Miller et al. |
| 4,859,462 A | 8/1989 | Chow et al. |
| 4,877,629 A | 10/1989 | Stypula et al. |
| 4,892,741 A | 1/1990 | Ohm et al. |
| 4,900,557 A | 2/1990 | Dell et al. |
| 4,910,028 A | 3/1990 | Bernacchi et al. |
| 4,913,919 A | 4/1990 | Cornwell et al. |
| 4,915,954 A | 4/1990 | Ayer et al. |
| 4,959,227 A | 9/1990 | Amer ........ 426/35 |
| 4,980,193 A | 12/1990 | Tuason et al. |
| 4,981,698 A | 1/1991 | Cherukuri et al. |
| 4,981,707 A | 1/1991 | Morris |
| 4,983,399 A | 1/1991 | Maish |
| 4,994,276 A | 2/1991 | Baichwal et al. ........ 424/440 |
| 5,006,513 A | 4/1991 | Hector et al. ........ 514/43 |
| 5,008,113 A | 4/1991 | Kokubo et al. |
| 5,008,117 A * | 4/1991 | Calanchi et al. ........ 424/494 |
| 5,009,897 A | 4/1991 | Brinker et al. |
| 5,011,701 A | 4/1991 | Baer et al. |
| 5,023,083 A | 6/1991 | Drell ........ 424/439 |
| 5,024,842 A | 6/1991 | Edgren et al. |
| 5,059,248 A | 10/1991 | Signorino et al. |
| 5,068,110 A | 11/1991 | Fawzi et al. |
| 5,089,270 A | 2/1992 | Hampton et al. |
| 5,098,715 A | 3/1992 | McCabe et al. |
| 5,122,385 A | 6/1992 | Daher et al. |
| 5,128,143 A | 7/1992 | Baichwall et al. ........ 424/464 |
| 5,192,569 A | 3/1993 | McGinley et al. |
| 5,194,464 A | 3/1993 | Itoh et al. |
| 5,202,137 A | 4/1993 | Duffy et al. |
| 5,209,942 A | 5/1993 | Bauer et al. ........ 426/605 |
| 5,213,738 A | 5/1993 | Hampton et al. |
| 5,225,202 A | 7/1993 | Hodges et al. |
| 5,262,173 A | 11/1993 | Sheth et al. ........ 424/494 |
| 5,268,182 A | 12/1993 | Brinker et al. |
| 5,286,502 A | 2/1994 | Meyers |
| 5,286,510 A | 2/1994 | Bauer |
| 5,288,501 A | 2/1994 | Nürnberg et al. |
| 5,306,506 A | 4/1994 | Zema et al. |
| 5,310,572 A | 5/1994 | Woodard et al. |
| 5,332,595 A | 7/1994 | Gaonkar |
| 5,358,990 A | 10/1994 | Woodard et al. |
| 5,366,742 A | 11/1994 | Tuason, Jr. et al. |
| 5,368,840 A | 11/1994 | Unger ........ 424/9 |
| 5,376,388 A | 12/1994 | Meyers |
| 5,389,129 A | 2/1995 | Jordan |
| 5,393,333 A | 2/1995 | Trouve |
| 5,401,515 A | 3/1995 | Woodard et al. |
| 5,409,715 A | 4/1995 | Meyers |
| 5,411,746 A | 5/1995 | Signorino et al. |
| 5,429,830 A | 7/1995 | Janovsky et al. |
| 5,435,840 A | 8/1995 | Hilborn et al. |
| 5,458,887 A | 10/1995 | Chen et al. |
| 5,470,581 A | 11/1995 | Grillo et al. |
| 5,470,603 A | 11/1995 | Staniforth et al. |
| 5,472,710 A | 12/1995 | Klokkers-Bethke et al. |
| 5,472,712 A | 12/1995 | Oshlack et al. ........ 424/480 |
| 5,480,479 A | 1/1996 | Signorino |
| 5,512,092 A | 4/1996 | Maruyama et al. |
| 5,512,314 A | 4/1996 | Signorino et al. |
| 5,514,384 A | 5/1996 | Signorino |
| 5,514,435 A | 5/1996 | Suzuki et al. ........ 428/40 |

| | | | | | | |
|---|---|---|---|---|---|---|
| 5,523,293 A | 6/1996 | Jane et al. | | EP | 0648487 | 4/1995 |
| 5,529,783 A | 6/1996 | Burke et al. ............... 424/441 | | EP | 0663820 | 7/1995 |
| 5,547,948 A | 8/1996 | Barcomb | | EP | 0684042 | 11/1995 |
| 5,560,930 A | 10/1996 | Maruyama et al. | | EP | 0707475 | 4/1996 |
| 5,580,580 A | 12/1996 | Masterson et al. | | EP | 0 714 656 | 6/1996 |
| 5,591,455 A | 1/1997 | Signorino | | EP | 0737472 | 10/1996 |
| 5,595,592 A | 1/1997 | Signorino et al. | | EP | 0746310 | 12/1996 |
| 5,595,762 A | 1/1997 | Derrieu et al. | | EP | 0751837 | 1/1997 |
| 5,624,612 A | 4/1997 | Sewall et al. | | EP | 0788790 | 8/1997 |
| 5,629,003 A | 5/1997 | Horstmann et al. | | EP | 0 795 324 | 9/1997 |
| 5,630,871 A | 5/1997 | Jordan | | EP | 0 829 478 A2 | 3/1998 |
| 5,656,080 A | 8/1997 | Staniforth et al. | | EP | 0839527 | 5/1998 |
| 5,662,732 A | 9/1997 | Kelley et al. | | EP | 0852141 | 7/1998 |
| 5,663,198 A | 9/1997 | Reul et al. ............... 514/479 | | EP | 0592130 | 4/1999 |
| 5,683,722 A | 11/1997 | Derrieu et al. | | EP | 0974366 | 1/2000 |
| 5,695,784 A | 12/1997 | Pöllinger et al. | | EP | 1010423 | 6/2000 |
| 5,700,929 A | 12/1997 | Kokubo et al. | | EP | 1101490 | 5/2001 |
| 5,709,896 A | 1/1998 | Hartigan et al. ............ 426/103 | | FR | 2 404 029 | 4/1979 |
| 5,733,575 A | 3/1998 | Mehra et al. | | GB | 734414 | 1/1956 |
| 5,741,600 A | 4/1998 | Olson | | GB | 1371840 | 10/1974 |
| 5,743,947 A | 4/1998 | Jordan | | GB | 1594102 | 9/1977 |
| 5,756,123 A | 5/1998 | Yamamoto et al. | | GB | 1 581 841 | 12/1980 |
| 5,759,576 A | 6/1998 | Barcomb | | GB | 5 594 102 | 7/1987 |
| 5,759,577 A | 6/1998 | Barcomb | | GB | 2 212 396 | 7/1989 |
| 5,780,057 A | 7/1998 | Conte et al. ............... 424/468 | | JP | 51123815 | 4/1975 |
| 5,840,332 A | 11/1998 | Lerner et al. | | JP | 52117413 | 3/1976 |
| 5,849,320 A | 12/1998 | Turnblad et al. | | JP | 1774819 | 3/1985 |
| 5,851,579 A | 12/1998 | Wu et al. | | JP | 5-29205 | 10/1985 |
| 5,876,739 A | 3/1999 | Turnblad et al. | | JP | 6132289 | 7/1986 |
| 5,882,707 A | 3/1999 | Grillo | | JP | 6-62400 | 5/1987 |
| 5,885,617 A | 3/1999 | Jordan | | JP | 62-111917 | 5/1987 |
| 6,030,641 A | 2/2000 | Yamashita et al. | | JP | 118057 | 4/1989 |
| 6,039,976 A | 3/2000 | Mehra et al. | | JP | 2511577 | 2/1993 |
| 6,153,601 A | 11/2000 | Breton et al. | | JP | 2134366 | 3/1995 |
| 6,228,398 B1 | 5/2001 | Devane et al. | | JP | 873379 | 3/1996 |
| 6,270,830 B1 | 8/2001 | Kamada et al. | | JP | 8109126 | 4/1996 |
| 6,274,162 B1 | 8/2001 | Steffenino et al. | | JP | 2646851 | 5/1997 |
| 6,294,195 B1 | 9/2001 | Oshlack et al. | | JP | 1899661 | 4/1998 |
| | | | | JP | 11315032 | 2/1999 |
| | | | | JP | 1160472 | 3/1999 |

FOREIGN PATENT DOCUMENTS

| | | | | | | |
|---|---|---|---|---|---|---|
| EP | 0063014 | 8/1985 | | JP | 11116467 | 4/1999 |
| EP | 0153104 | 8/1985 | | JP | 11315032 | 11/1999 |
| EP | 0 171 457 | 2/1986 | | JP | 11322624 | 11/1999 |
| EP | 0 181 650 | 5/1986 | | WO | WO 84/02843 | 8/1984 |
| EP | 0 197 571 B1 | 10/1986 | | WO | WO 85/01207 | 3/1985 |
| EP | 0 226 671 | 7/1987 | | WO | WO 86/06626 | 11/1986 |
| EP | 0020496 | 1/1988 | | WO | WO 88/01506 | 3/1988 |
| EP | 0 255 725 | 2/1988 | | WO | WO 88/03795 | 6/1988 |
| EP | 0256538 | 2/1988 | | WO | WO 90/03165 | 4/1990 |
| EP | 0305051 | 1/1989 | | WO | WO 90/11754 | 10/1990 |
| EP | 0339811 | 11/1989 | | WO | WO 9114729 | 10/1991 |
| EP | 0 347 748 | 12/1989 | | WO | WO 91/15548 | 10/1991 |
| EP | 0360562 | 3/1990 | | WO | WO 9209273 | 6/1992 |
| EP | 0 181 650 | 8/1990 | | WO | WO 92/11002 | 7/1992 |
| EP | 0222856 | 12/1990 | | WO | WO 92/15288 | 9/1992 |
| EP | 0425154 | 5/1991 | | WO | WO 93/09785 | 5/1993 |
| EP | 0434321 | 6/1991 | | WO | WO 93/15719 | 8/1993 |
| EP | 0443572 | 8/1991 | | WO | WO 93/19061 | 9/1993 |
| EP | 0 453 001 | 10/1991 | | WO | WO 9320709 | 10/1993 |
| EP | 0460185 | 12/1991 | | WO | WO 9320711 | 10/1993 |
| EP | 525389 | 6/1992 | | WO | WO 93/25238 | 12/1993 |
| EP | 0497331 | 8/1992 | | WO | WO 94/03160 | 2/1994 |
| EP | 0245855 | 1/1993 | | WO | WO 95/08993 | 4/1995 |
| EP | 0527637 | 2/1993 | | WO | WO 95/11667 | 5/1995 |
| EP | 0550737 | 7/1993 | | WO | WO95/22962 | 8/1995 |
| EP | 595110 | 10/1993 | | WO | WO 9528918 | 11/1995 |
| EP | 0567541 | 11/1993 | | WO | WO 9601874 | 1/1996 |
| EP | 0 600 775 | 6/1994 | | WO | WO 96/10995 | 4/1996 |
| EP | 0 627 173 A1 | 7/1994 | | WO | WO 96/16664 | 6/1996 |
| EP | 0 627 173 | 12/1994 | | WO | WO 96/29058 | 9/1996 |
| EP | 0 630 646 | 12/1994 | | WO | WO 96/30011 | 10/1996 |

| | | |
|---|---|---|
| WO | WO 96/33700 | 10/1996 |
| WO | WO96/35413 | 11/1996 |
| WO | WO96/35516 | 11/1996 |
| WO | WO 97/02038 | 1/1997 |
| WO | WO97/09967 | 3/1997 |
| WO | WO 97/15191 | 5/1997 |
| WO | WO 97/16172 | 5/1997 |
| WO | WO 97/18839 | 5/1997 |
| WO | WO97/23564 | 7/1997 |
| WO | WO 97/25979 | 7/1997 |
| WO | WO 97/34580 | 9/1997 |
| WO | WO 9737638 | 10/1997 |
| WO | WO 97/49301 | 12/1997 |
| WO | WO 98/06260 | 2/1998 |
| WO | WO 98/17126 | 4/1998 |
| WO | WO 9953899 | 4/1998 |
| WO | WO 98/20861 | 5/1998 |
| WO | WO 98/21203 | 5/1998 |
| WO | WO98/30341 | 7/1998 |
| WO | WO 98/43673 | 10/1998 |
| WO | WO 98/55148 | 12/1998 |
| WO | WO 9902135 | 1/1999 |
| WO | WO99/03449 | 1/1999 |
| WO | WO 9907347 | 2/1999 |
| WO | WO 9908658 | 2/1999 |
| WO | WO 99/10017 | 3/1999 |
| WO | WO 9918938 | 4/1999 |
| WO | WO 99/20261 | 4/1999 |
| WO | WO 99/20271 | 4/1999 |
| WO | WO 99/22769 A1 | 5/1999 |
| WO | WO99/24020 | 5/1999 |
| WO | WO 9938495 | 8/1999 |
| WO | WO 99/43343 | 9/1999 |
| WO | WO 99/49835 | 10/1999 |
| WO | WO 99/49895 | 10/1999 |
| WO | WO 99/51089 | 10/1999 |
| WO | WO 99/53899 | 10/1999 |
| WO | WO 9955313 | 11/1999 |
| WO | WO 99/55704 | 11/1999 |
| WO | WO 99/56761 | 11/1999 |
| WO | WO 0001370 | 1/2000 |
| WO | WO 0010538 | 3/2000 |
| WO | WO 0018374 | 4/2000 |
| WO | WO 0028974 | 5/2000 |
| WO | WO 0126633 | 10/2000 |
| WO | WO 0074655 | 12/2000 |
| WO | WO 0103677 | 1/2001 |

OTHER PUBLICATIONS

Lee, J.T., "Evaluation of the functional stability of microcrystalline cellulose (MCC): carrageenan conventional aqueous film coating," *Annual Meeting*, Nov. 14–18, 1999, AAPS Abstract No. 3459, 1 page.

Ritschel, "Die Tablette," Der Pharmazeutische Betrieb, 1966, 7, 41–48 and 366–371.

Rothe & Groppenbacher, "Filmdragierung auf waBriger Basis," Die Pharmazeutische Industrie, 1972, 34(892–894), 3–8.

Rothe & Groppenbacher, "Filmdragierung nach dem Tauchrohr–Verfahren," Die Pharmazeutische Industrie, 1973, 35(723–729), 3–12.

* cited by examiner

EDIBLE COATING COMPOSITION

This application is a continuation-in-part of U.S. patent application Ser. No. 09/491,724, now U.S. Pat. No. 6,432,448, filed Jan. 27, 2000, which claims the benefit of prior U.S. provisional application, No. 60/119,005, filed Feb. 8 1999, Ser. No. 60/133,092, filed May 7, 1999, Ser. No. 60/162,514, filed Oct. 29, 1999, Ser. No. 60/167,407, filed Nov. 24, 1999, and Ser. No. 60/172,526, filed Dec. 17, 1999.

FIELD OF THE INVENTION

This invention relates to edible, hardenable, prompt release coating compositions comprising microcrystalline cellulose (MCC), carrageenan (CGN) and at least one of a strengthening polymer or a plasticizer. The coatings of the present invention can be applied to pharmaceutical, including nutriceutical, and veterinary solid dosage forms, confectionery, seeds, animal feed, fertilizers, pesticide tablets and granules, and foods, are readily dispersed in aqueous media, and, when applied as a coating and ingested by, for example, a human, do not significantly retard or extend release of active ingredient(s) from a substrate coated therewith.

BACKGROUND OF THE INVENTION

It is a common practice to coat pharmaceutical and veterinary tablets to obtain several advantages. Among these are to mask unpleasant tasting active ingredients with a barrier coat, to improve the surface characteristics of tablets to make them easier to swallow, to reduce the absorption of water or moisture which can potentially degrade the active ingredient or promote some other undesirable change in the tablet structure, and simply to make a more elegant appearing tablet.

Another very important function of a pharmaceutical or veterinary tablet coating is to improve the integrity of the tablet itself. Uncoated tablets are often subject to being abraded or chipped, causing a loss of active ingredient in the process. More dramatically, they may break into two or more pieces. One measure of a useful coating is its ability to prevent any of these physical degradations of tablet structure. The effectiveness of a coating material to prevent abrading, chipping, or breakage of the tablet is determined by friability testing.

Confectionery and foods may be coated with a formulation to preserve the confection or food from deteriorating by contact with the oxygen and the moisture in the atmosphere. Coatings also can provide improved appearance and desirable organoleptic properties to the food as well as preventing loss of flavor.

Seeds may be coated to preserve the viability of the seeds by protecting against moisture. They may also be coated as a means for increasing particle size to facilitate mechanical planting. A dye can be included in the coating formulation to identify the seeds as to quality, type, or some other designation. Frequently, a pesticide, e.g., a fungicide, is incorporated into the coating formulation to protect both the seed itself and the seedling that results from germination of the seed. In all cases, this coating must not decrease the viability of the seeds or interfere with germination when the seeds are planted in the soil.

Animal feed may be coated to improve its flowability, appearance and its resistance to powdering or dusting. In such applications, the coating may be formulated to include vitamins, hormones, antibiotics, or the like, to benefit the livestock which will consume the feed.

Fertilizers, in either granular or tableted forms, may be coated to retain the integrity of the form and, especially, to protect the fertilizer from moisture which can cause agglomeration during storage, which could make rapid, even application to the soil difficult or inconvenient.

Coating of tableted pesticide formulations serves to maintain the integrity of the tablets or granules until they are placed in water where they rapidly disintegrate, forming a solution or slurry to be applied to the soil or plants. A second, and equally important, function of the coatings on tablets containing pesticides is to prevent human contact with the pesticide, thereby increasing safety for those handling and applying the pesticide.

Currently, most commercially available edible coatings utilize a synthetic cellulosic polymer such as hydroxypropylmethylcellulose (HPMC). Other synthetic film-formers which are commonly used include ethylcellulose, methylcellulose, polyvinylpyrrolidone, and polydextrose. These coating materials may be used alone or in combination with secondary film-formers such as sodium alginate or propylene glycol alginate. The foregoing are usually used in combination with other ingredients including fillers, for example, lactose or maltodextrin; plasticizers, such as polyethylene glycols, dibutyl sebacate, and triethyl citrate; surfactants; and often coloring materials such as a food dye or pigment, including opacifiers such as titanium dioxide and the like.

In the preparation of a coating formulation to be sprayed, the film former is usually dissolved or dispersed in a solvent, for example, water, along with the other ingredients of the formulation. In aqueous systems, since many polymers require significant time to become fully hydrated, the coating formulation must frequently be prepared in advance of the time it is to be applied to the tablets. A common procedure is to prepare these coating formulations the day preceding the coating operation in order to assure adequate hydration of the polymers used in them.

A particular disadvantage of coatings based primarily on HPMC is that the coating may harden over time and therefore increase tablet disintegration times. An increase in disintegration time delays the bioavailability of the active ingredient at least in proportion to the increase in disintegration time. Many other agents commonly used in coating compositions are also known to delay release of pharmaceutical agents, such as enteric coatings which use polymeric film forming materials which are insoluble in water, or gastric fluid, some of these being specifically selected to by-pass both the stomach and small intestine and provide colonic release.

The coatings of this invention meet U.S. Pharmacopoeia standards for rapid or immediate dissolution (U.S.P. monograph 23) of active ingredients from tablets or other solid dosage forms coated with them. They provide prompt release or dissolution consistent with the release rates which is normally obtained with the uncoated tablets or other substrates. Thus, they do not adversely impact or retard release of active ingredients from a substrate coated with them. Further, the coatings of this invention are readily dispersed and rapidly hydrated in aqueous media for application to a coating substrate, and provide elegant coatings which have all the benefits of coatings now in commercial use without the drawbacks that are common to them.

SUMMARY OF THE INVENTION

It has been found that these and other advantages may be achieved in accordance with the present invention by a coating composition which comprises a unique combination of materials specifically adapted for a prompt release when placed aqueous media or ingested, e.g., by a human. The coating composition of the present invention comprises microcrystalline cellulose, carrageenan, and at least one of a strengthening polymer and a plasticizer. More specifically, the present invention provides a prompt release, edible, hardenable coating composition comprising 3% to 40% microcrystalline cellulose, 9% to 25% iota carrageenan, and at least one of a strengthening polymer, a plasticizer, or a surface active agent, as well as to dry coatings and aqueous dispersions thereof.

The present invention also provides pharmaceutical, including neutriceutical, and veterinary solid dosage forms, confectionery, seeds, animal feed, fertilizers, pesticide tablets and granules, and foods coated with the prompt release edible, hardenable composition of this invention.

DETAILED DESCRIPTION OF THE INVENTION

For purposes of this application, the term "edible" is intended to mean food grade materials which are approved by regulatory authorities for use in pharmaceutical or food applications. The term "hardenable" used to describe the coating compositions of this invention is intended to include only those coating compositions that are capable of being dried from an aqueous solution or dispersion thereof into a solid coating which resists abrasive forces, i.e. a hardened coating, as distinguished from those "enrobing" coatings on confections which set up into a soft coating that can be handled and packaged but which do not resist abrasive forces significantly. The terms "immediate", "rapid" or "prompt" release as applied to dissolution rates or times for the coating compositions of this invention or tablets coated with the compositions of this invention means that the coatings of this invention meet U.S. Pharmacopoeia standards (U.S.P. monograph 23) for rapid or immediate dissolution of active ingredients from tablets or other solid dosage forms coated therewith. Thus, they provide prompt release or dissolution consistent with the release rates which is normally obtained with the uncoated tablets or other substrate. They do not, consistent with the pharmacopeia standards above, when placed in aqueous media or ingested by, e.g., a human, significantly impact or retard release or dissolution of tablets or other solid dosage forms coated therewith. For example, coatings made in accordance with the present invention are substantially or completely disintegrated and/or dissolved within less than 10 minutes after being ingested or placed in aqueous media. Thus, when a pharmaceutical solid dosage form is coated with the coating of this invention and ingested by a human or other animal, the coating of this invention is dissolved or disintegrated prior to leaving the stomach. In the specification, examples and claims which follow, all percentages are by dry weight of the composition. These definitions are intended to apply throughout this application unless a contrary meaning is clearly indicated.

The microcrystalline cellulose, either coprocessed with carrageenan or simply blended therewith, interacts with the carrageenan to provide important film-forming characteristics required to provide an elegant coating which is particularly useful in, for example, coating pharmaceutical and veterinary tablets, caplets, granules, and spheres which contain active ingredients which require release promptly after being placed in aqueous media or ingested.

Microcrystalline cellulose is a purified, partially depolymerized cellulose that is generally produced by treating a source of cellulose, preferably alpha cellulose in the form of a pulp from fibrous plants, with a mineral acid, preferably hydrochloric acid. The acid selectively attacks the less ordered regions of the cellulose polymer chain, thereby exposing and freeing the crystallite sites, forming the crystallite aggregates which constitute microcrystalline cellulose. These are then separated from the reaction mixture and washed to remove degraded by-products. The resulting wet mass, generally containing 40 to 60 percent moisture, is referred to in the art by several names, including hydrolyzed cellulose, microcrystalline cellulose, microcrystalline cellulose wetcake, or simply wetcake. This microcrystalline cellulose wetcake may be used as such or may be further modified, for example, by attrition and/or drying, and utilized in accordance with the present invention.

Microcrystalline cellulose may also be produced for use in the present invention using a steam explosion treatment. In this process, wood chips or other cellulosic materials are placed in a chamber into which super-heated steam is introduced. After being maintained for a period of about 1–5 minutes, the exit valve is opened rapidly, releasing the contents explosively and yielding microcrystalline cellulose. No additional acid need be introduced into the reaction mixture, since it is believed that the acidic materials in the wood chips and the elevated temperature and pressure hydrolyze the cellulose and degrade it. In addition to the specific forms of microcrystalline cellulose, the present invention also contemplates the use of other cellulose derivatives, including microreticulated cellulose, also known as microreticulated microcrystalline cellulose, and powdered cellulose such as a commercial material sold as "Solka Floc®." As discussed in greater detail below, the microcrystalline cellulose preferred for use in the present invention is microcrystalline cellulose which has an average particle size below about 100 microns, preferably microcrystalline cellulose which been attrited or has an average particle size in the range of 1 to 50 microns, preferably 1 to 30 microns.

Carrageenan is used in combination with microcrystalline cellulose to form the elegant prompt release coatings of the present invention. Carrageenan for use in the present invention is a naturally derived carrageenan, including the grades further defined below as iota, kappa, and lambda carrageenan. The preferred type of carrageenan, a polysaccharide which is comprised of repeating galactose units and 3,6-anhydrogalactose units, that is suitable for the compositions of this invention is referred to as iota carrageenan. A rich source of iota carrageenan is the seaweed *Eucheuma spinosum*. The approximate content of anhydrogalactose units in iota carrageenan is 30% whereas kappa carrageenan has 34% anhydrogalactose units and lambda carrageenan is essentially devoid of these units. Carrageenans are also characterized by the amount of ester sulfate groups that are present on both the galactose and anhydrogalactose units. The ester sulfate content of iota carrageenan may range from about 25% to 34%, preferably about 32%. This is intermediate between kappa carrageenan which has a 25% ester sulfate content and lambda carrageenan which has a 35% ester sulfate content. The sodium salt of iota carrageenan is soluble in cold water, but different grades of iota carrageenan require heating water to different temperatures to dissolve them. The iota carrageenans which are suitable for the microcrystalline cellulose/iota carrageenan material of this invention are soluble in water heated up to 80° C. (176° F.). Preferred grades of iota carrageenan are soluble at lower temperatures, for example, at 50° C. (122° F.), including but not limited to sodium iota carrageenan.

In the coating compositions of this invention, a film forming amount of carrageenan must be employed. A suitable film forming amount of carrageenan is generally in the range of about 9% to about 25% by dry weight of the coating composition, advantageously in the range of about 10% to about 20% of the dry weight of the composition.

The microcrystalline cellulose and carrageenan may be coprocessed or may be blended in any suitable manner, such as dry blending.

Coprocessed microcrystalline cellulose/iota carrageenan is rapidly peptizable. Peptization means that the dry agent can readily be dispersed in water in a colloidal state. Peptization of a dry agent in aqueous media allows the functionality of the agent to be restored to a level near or preferably at the level observed before the agent was dried. Rapidly peptizable dry agents can be dispersed (peptized) in a colloidal state with minimal agitation. Thus, the novel coating formulations in which the coprocessed microcrystalline cellulose/iota carrageenan is incorporated can be hydrated in as little as 0.5 hour, but more preferably require 1 to 3 hours. The common practice of preparing the coating formulation on the preceding day may be avoided, although it may also be continued, if this is preferable, without harming the formulation. If the formulation is prepared on one day and then used the next day, prior to being used, the formulation must be stirred for a short while to restore it to its flowable state.

The coprocessed microcrystalline/iota carrageenan compositions useful in this invention may be prepared by first attriting hydrolyzed cellulose wetcake, such that the average particle size of the wetcake particles is generally not more than about 20 microns, preferably less than about 10 microns, dispersing the attrited wetcake in water heated to a temperature above the temperature at which the particular grade of iota carrageenan being used dissolves, adding the dry carrageenan to the dispersion of microcrystalline cellulose, mixing the components, preferably homogenizing the mixture to assure intimate mixing, and drying the dispersion. Spray-drying is normally used to prepare the dried materials useful in this invention, but other methods of drying the dispersion may equally be acceptable.

It is possible to prepare the coatings directly, that is, before the drying of the wetcake, from a dispersion of microcrystalline cellulose wetcake and the carrageenan by accounting for the water present in the wetcake and adding the other ingredients in the formulation to this dispersion. Although this method of operation may be preferred for some coating operations, it is usually preferable to use the spray-dried, or otherwise dried, material because transportation costs for a dispersion would be less economical. Furthermore, drying by any method may enhance the association of the microcrystalline cellulose with the carrageenan, which may result in a more satisfactory prompt release coating.

Dry blended microcrystalline cellulose (e.g., Avicel® PH-105, average particle size 20 microns) and iota carrageenan, has been found to provide coating compositions that are at least equal to, and in some cases, superior to, coating compositions prepared from coprocessed microcrystalline cellulose/carrageenan.

Carrageenan by itself is known to be a natural film forming hydrocolloid when an aqueous dispersion thereof is spread on a surface and allowed to dry. However, the film is considered to be too weak for pharmaceutical tablets as shown by the results in Comparative Example A and therefore requires the presence of microcrystalline cellulose for satisfactory results.

A dry, physical blend of iota carrageenan and microcrystalline cellulose (Avicel® PH-102, average particle size 100 microns) also yielded what appear to be commercially unsatisfactory results in Comparative Example B. Thus, for commercial purposes, it is believed that the average particle size of the microcrystalline cellulose used in a dry blend with the natural, film forming hydrocolloid should be below 100 microns, advantageously below about 50 microns, preferably in the range of about 1–50 microns, more preferably, about 1–30 microns. Elegant, high performance coating formulations within the scope of this invention may be prepared from such dry, physical blends of microcrystalline cellulose and carrageenan.

A wide range of weight ratios of microcrystalline cellulose to carrageenan of from 90:10 to about 15:85 may be employed in this invention. In those applications which require a higher ratio microcrystalline cellulose to carrageenan in the MCC:CGN weight ratio generally ranges from about 90:10 to about 60:40, particularly from about 85:15 to about 65:35, more particularly, approximately 70:30. In certain embodiments of this invention it has been found that relatively lesser amounts of microcrystalline cellulose can be employed, such that the ratio of MCC:CGN can be in the range of from about 15:85 up to 60:40, preferably up to 55:45, and most preferably up to 50:50. A particular advantage for the dry, physical blends is that the ratio can be easily changed by simple blending techniques rather than manufacturing different ratios of coprocessed material. Thus, the dry, physical blends provide significantly greater flexibility for specific applications having different requirements. Pharmaceutical and veterinary solid dosage forms containing certain active ingredients may require increased carrageenan content in the composition to ideally coat the tablets. For these pharmaceutical and veterinary applications, a preferred weight ratio of microcrystalline cellulose to carrageenan is in the range of about 75:25 to about 25:75.

Regardless of whether the composition is based on coprocessed microcrystalline cellulose/carrageenan or a dry, physical blend of microcrystalline cellulose and carrageenan, a strengthening polymer, preferably, hydroxyethylcellulose (HEC) or polyvinylpyrrolidone (PVP), a plasticizer or both a strengthening polymer and a plasticizer and/or a surface active agent may be present in the coating formulation of this invention.

Other strengthening polymers which can provide the same benefit and may be used instead of HEC include HPMC, hydroxypropylcellulose, ethylcellulose, and methylcellulose; however, care must be exercised in the use of such alternative materials to avoid significantly retarding release of active ingredients and/or bioavailability. The preferred amount of strengthening polymer is less than the total amount of microcrystalline cellulose and carrageenan present in the composition. Depending on the desired hardness of the coating, the strengthening polymer may be employed in the composition at a level of about 0.5% to about 30%, to provide strength and improved appearance to the coating. This strength can be demonstrated by casting films of coating formulations on a flat, non-adherent surface, cutting strips of uniform width from the casting, and subjecting the strips to tensile testing on, e.g., an Instron Tensile Tester. The results of these tests show a very significant increase in tensile strength and decreased brittleness of the film when HEC or another strengthening polymer is included in the formulation. Strengthening polymers suitable for use in this invention and which will not significantly retard release from tablets or other solid dosage forms, are those polymers having a viscosity equal to or less than 20 mPa·s in a 2% aqueous solution at 20° C. When a strengthening polymer is employed in the formulation in absence of a plasticizer, it is generally employed at about 5% to about 30% by dry weight coating composition.

In a preferred composition a conventional plasticizer is also included in the coating composition. Suitable plasticizers include polyethylene glycol, advantageously a high molecular weight polyethylene glycol, triacetin, dibutyl sebacate, propylene glycol, sorbitol, glycerin, and triethyl citrate. Of these, polyethylene glycol is preferred. These plasticizers may be employed in the coating compositions of the invention at a level of 18% to about 36% by dry weight of the coating composition, most preferably at a level of 31% to 35% by dry weight of the coating composition.

The prompt release coating compositions of the invention may include at least one filler. Such fillers may include, for example, calcium carbonate, dicalcium phosphate and carbohydrates, such as starch, maltodextrin, lactose, mannitol and other sugars. Of these, maltodextrin, mannitol and lactose are preferred fillers.

The prompt release coating compositions of the invention may include at least one surfactant. Such surfactants include either anionic or nonionic surfactants. Useful surfactants may be, e.g., sodium lauryl sulfate, hydroxylated soy lecithin (lecithin), polysorbates, and block copolymers of propylene oxide and ethylene oxide. Lecithin has been found to be particularly desirable in certain coating compositions of this invention and is suitably utilized at a level of about 2% to about 10% by dry weight of the formulation.

Coloring agents and opacifiers may also be used in these coatings or added to a suspension thereof including aluminum lakes, insoluble pigments, water-soluble dyes, titanium dioxide, and talc. Stearic acid or a salt or ester thereof, may be included at a level of about 1% to about 5% by dry weight of the composition to increase gloss of the coating, particularly when a plasticizer is not employed in the composition. Likewise propylene glycol alginate, may be used in small quantities (about 5% to about 10% by dry weight of the composition) to increase the gloss of the coating, as shown in Example 31.

A coating formulation of this invention may be sold as a dry powder formulation or as a ready-to-use dispersion in water. For aqueous dispersions it is preferred that these be prepared under aseptic conditions. Heating the water to an elevated temperature, for example, 85° C., prior to preparation of the dispersion has shown that bacteria, mold, and yeast growth are prevented for at least 48 hours on agar pour plates. Therefore, if the containers for the dispersion are properly sanitized and then kept closed after being filled until they are used, there is little likelihood of bacteria, mold, or yeast growing in the dispersion. Alternatively, if a formulation is to be sold as an aqueous dispersion to be stored for a period of time, a preservative may be added. A combination of methyl paraben and propyl paraben has been found to be useful in this regard.

On a dry weight percentage basis a preferred composition of this invention comprises at least about 43%, suitably about 45% to about 75% of microcrystalline cellulose and carrageenan powder combined, more preferably about 45% to about 60%; about 0.5% to about 30% of strengthening polymer, more preferably about 7% to about 22%; and about 25% to about 40% of plasticizer, more preferably about 31% to about 35%; and an inert filler at about 2% to about 28%. Optionally, about 1% to about 30% of the formulation may comprise edible coloring agents and opacificiers such as talc or titanium dioxide, including from 1% to about 8% of coloring component such as a food dye or pigment, preferably about 1% to about 3%. Other optional ingredients may include a surfactant at about 0.5% to about 10%, advantageously 0.5 to about 7%, preferably 1.25% to 3% when a filler such as maltodextrin or mannitol is present. When no filler is employed higher amounts of surfactants such as lecithin may be employed at a level of about 5% to about 20%. Preservatives, such as methyl paraben at 0.75% to 1.50% and/or propyl paraben at 0.075% to 0.15% may also be present in the formulation. When maltodextrin is the filler, it is generally employed at about 2% to about 7% by dry weight of the composition, whereas when mannitol is the filler it is generally employed at about 10% to about 25% by dry weight of the formulation. These fillers may be employed alone or in combination within the ranges specified above.

The low level of fillers present in these coating formulations, particularly when the opacifier is titanium dioxide, enables the formulator to utilize relatively small amounts of coloring agent. Since coloring agents are quite costly, this provides a significant cost reduction from those formulations requiring from 6% to about 16% to effectively color prior art coating formulations.

Several other embodiments of this invention may be specifically mentioned as being of special interest to this invention, in which there is provided an edible, hardenable, prompt release coating composition comprising about 3% to 40% microcrystalline cellulose in combination with about 9% to about 25% iota carrageenan and at least one of a strengthening polymer, a plasticizer, or a surface active agent, wherein said coating composition is rapidly hydratable and does not, when ingested or placed in an aqueous medium, significantly retard release of active ingredients from a substrate to which said coating is applied. Any of the strengthening polymers, plasticizers, surface active agents, coloring agents, etc, set forth herein, may be used in this embodiment.

For example, a first of these embodiments comprises an edible, hardenable, prompt release coating composition comprising about 5% to about 25%, more particularly about 5% to 10%, microcrystalline cellulose; about 10% to about 16%, more specifically about 14% to 16%, iota carrageenan. Such embodiments may also contain about 2% to about 10% of a surface active agent such as lecithin, about 35% to about 70% of a filler such as lactose as a filler and/or about 5% to about 10% propylene glycol alginate. These compositions my also contain 5% to 22% of a strengthening polymer such as polyvinylpyrrolidone or hydroxyethylcellulose. A mixture of strengthening polymers such as PVP and HEC may also be employed. In addition, from about 2% to 10% of a coloring agent may be included to provide pigmented coating composition. These compositions may also contain at least one filler such as maltodextrin, dicalcium phosphate, croscarmellose sodium and a mixture thereof. In this embodiment a reduced level of microcrystalline cellulose may be employed together with a small amount of surface active agent, with a high level of lactose used as the filler. Such a particular composition may comprise 5% to 10% microcrystalline cellulose, 14%to 16% iota carrageenan, 2% to 4% hydroxylated soy lecithin, 65% to 70% lactose, and may include from about 5% to about 10% propylene glycol alginate. The MCC:CGN weight ratio in this embodiment may be in the range of about 15:85 up to 60:40, or more particularly 15:85 to about 50:50; and the combined total of microcrystalline cellulose and carrageenan comprises from about 20% to about 40% of the coating composition. When PVP is used as the sole strengthening polymer, it is preferably employed at a level of about 5% to about 16%, whereas, when HEC is used as the sole strengthening polymer, it is preferably employed at a level of about 20% to about 22%. Specific examples of this embodiment are set forth as Examples 36–53 in Table 1 below.

A second of these embodiments of the coating composition of this invention comprises about 30% to about 40%, in particular about 33% to about 38%, microcrystalline cellulose; about 10% to about 20%, more specifically about 14% to about 17%, iota carrageenan, and about 12% to about 25%, more specifically about 12% to about 22% of a strengthening polymer such as hydroxyethylcellulose. These compositions may also further comprise about 5% to about 10%, more particularly 7% to 10%, of a surface active agent such as hydroxylated soy lecithin, about 8% to about 15% of a filler such as lactose, maltodextrin and a combination thereof, more particularly about 5% to about 10% lactose, and optionally from 5% to about 10% of a coloring agent. In this embodiment, if maltodextrin is the filler, it may be present at a level of about 3% to about 5%, specifically about 3%, in combination with a filler such as lactose at a level of about 7% to about 10%, more specifically about 8% to 9%. A suitable variation comprises compositions which, in addition to MCC, CGN and HEC, further comprise from about 30% to about 36, more particularly about 34% to about 35% polyethylene glycol and about 4% to about 5% coloring agent. In this group of compositions the weight ratio MCC:CGN may be in the range of about 60:40 to about 75:35, and the combined weight of MCC and CGN may be about 48% to about 60% by weight of the composition. It is also noted that this embodiment may contain a suitable coloring agent. This embodiment is illustrated in Examples 54–57 of Table 1 below.

Finally, a third embodiment of the composition of this invention comprises 30% to 40%, more specifically about 33% to about 38% microcrystalline cellulose, 10% to 20%, more specifically about 13% to about 16%, iota carrageenan, about 10% to about 15% of a strengthening polymer such as polyvinylpyrrolidone, and 30% to 40%, more specifically 33% to 36%, of a plasticizer such as polyethylene glycol. This embodiment may further comprise from about 2% to about 10% of a coloring agent. In this embodiment the weight ratio of MCC:CGN may be in the range of about 60:40 to about 75:25 and the combined weight of MCC and CGN comprises about 50% to about 60% by weight of the composition. A suitable coloring agent may be included in the compsotions of this embodiment. Example 58 of Table 1 illustrates this embodiment.

The viscosity of the hydrated formulation can be important. It ideally should be low enough to be pumped to a spray unit continuously and then sprayed evenly in a useful pattern onto the substrate being coated. A useful concentration of the dry ingredients in water on a weight percentage basis, therefore, may be about 6% to about 15%, advantageously 6.5% to 11%, preferably about 8% to about 11%. To assure uniformity of the coating composition, it may be preferable to maintain agitation of the aqueous dispersion during the entire period of its being sprayed onto the pharmaceutical or veterinary solid dosage forms, confectionery, seeds, animal feed, fertilizer, pesticide tablets, or food.

The preferred edible, hardenable, prompt release coating formulations of this invention may generally be prepared and used according to a simple procedure. A dry mixture of coprocessed microcrystalline cellulose/carrageenan powder or a dry blend of microcrystalline cellulose and carrageenan, and a strengthening polymer, such as hydroxyethylcellulose, polyethylene glycol or other acceptable plasticizer, optionally together with a solid filler such as maltodextrin, lactose, mannitol or the like, preservatives, and/or surfactants are blended to form dry coating composition. Addition of edible coloring agents, for example, a water-soluble dye or a pigment, may precede the hydration step required to prepare the final coating formulation. This dry mixture is then added slowly to the vortex of stirred, purified water. Stirring of this mixture is continued for a sufficient period to allow all of the components to be fully hydrated. If a colored coating material is required a water soluble dye or a pigment may also be added, preferably as a dispersion or solution, to the hydrated coating composition. Optionally surfactants, and/or plasticizers may also be added at this stage of the process.

In the formulations of microcrystalline cellulose and iota carrageenan, a simple propeller mixer provides adequate agitation for rapid hydration. The period of hydration may be as short as 0.5 hour. It may, and preferably should, be longer, but more than 3 hours is not believed to be necessary. Hydration can take place at room temperature or at elevated temperatures as high as 65.5° C. (150° F.), preferably at a temperature about 48.9° C. (120° F.). The time required for full hydration and the viscosity of the dispersion are both considerably reduced when the dispersion is prepared at an elevated temperature, but coating dispersions prepared at ambient temperature only require an increase in hydration time and a slight reduction in solids content to perform completely satisfactorily. As previously stated, these formulations may be prepared on the day preceding the coating operation, if that is more convenient; however, a period of mixing will be required to overcome the thixotropic behavior of a formulation which sets up during overnight storage. Unlike coating formulations based primarily on hydroxyalkyl ethers of cellulose, for example, HPMC, constant stirring of the microcrystalline and carrageenan-based formulations of this invention does not need to be continued throughout the coating procedure, but mixing may continue, if preferred.

Any commercial spray coater may be used to apply the coating. Examples of useful coaters are Vector High Coaters manufactured by Vector Corporation and Accela-Cota manufactured by Thomas Engineering. Equipment variables which one skilled in the art can manipulate to provide an elegant coating based on the microcrystalline cellulose and carrageenan materials, either coprocessed or dry blended, include inlet temperature, outlet temperature, air flow, speed of rotation of the coating pan, and the rate at which the coating formulation is pumped to the coater. It is important that the inlet and outlet temperatures be controlled so that they are high enough to efficiently dry the coating to prevent the tumbling action of the already-coated tablets from damaging the newly-applied coating before more coating is applied to the same tablets.

Hydroxyethylcellulose binds water more effectively than carrageenan does. Thus, the presence of the major amount of carrageenan in the formulations of this invention has a significant effect on the speed of drying of the edible coatings. Drying times are reduced considerably because of the presence of the carrageenan which dilutes the negative effect of HEC on drying time. Thus, in the case of low melting active pharmaceutical agents, for example, ibuprofen, the outlet temperature can be reduced and still provide short enough drying time to be commercially useful.

Hydroxyethylcellulose is particularly susceptible to clogging spray nozzles at high temperatures. An additional benefit provided by the formulations of this invention is the avoidance of clogging of the spray nozzles with dispersions being sprayed at high temperatures.

The level of coating applied to pharmaceutical or veterinary dosage forms is preferably between about 0.5% to about 4% by weight of the uncoated dosage form, more preferably about 2% to about 3.5%, by weight of the uncoated dosage form. This level of coating will provide an elegant, serviceable coating to a wide variety of dosage forms. To apply a heavier coating to tablets would not be economical, and it might adversely affect disintegration of the tablets or other properties. Too light a coating would not provide optimal properties normally expected from a coating, for example, improved friability or adequate taste masking.

For confections the coating level should be about 5% to about 10% by weight of the uncoated confection. Seed coatings should be in the range of about 3% to about 6% by weight of the uncoated seeds. Fertilizers and pesticide tablets and granules benefit from coating of 1% to about 3%, by weight of the uncoated granules or tablets.

From the following examples it has been shown that the coatings of the present invention may be applied successfully to tablets having a wide variety of active ingredients incorporated therein. For example, it has been reported that multivitamin tablets are difficult to coat because of the lipophilic surface properties of the vitamins. Similarly, ibuprofen is a challenging active ingredient to coat. Tablets comprising both of these difficult-to-coat active ingredients have been coated readily with the instant invention, providing elegant tablets. Additionally, the coatings have been applied to tablets which have been debossed with letters or a logo without bridging which would hide, or even obliterate, the debossed design.

An additional utility of the coating formulations of this invention is as a replacement for sugar coating of tablets. A sugar coating is applied primarily to increase the weight and/or size of the tablet, but this is an old art which presents numerous problems. It is, therefore, desirable to replace the traditional sugar coating with a more easily applied coating as shown in Example 26. This coating procedure has the additional advantage that no top coat is required to be applied as it is done with a sugar coating Storage of coated tablets under ambient temperature and humidity and 40° C. and 75% relative humidity for one to three months has demonstrated that no significant degradation has occurred. These tablets have disintegrated within the same length of time as the same batch of newly coated tablets did, and in each case provided dissolution rates and times substantially equal to those of the uncoated tablets used as a substrate for coating. This is an additional unexpected benefit of the coatings based on carrageenan and microcrystalline cellulose, and it differs from the known drawbacks of HPMC.

All components of the formulation are typically pharmaceutically acceptable, edible food grade materials.

The following examples, in which percentages are weight percent and tablet hardness is in Kiloponds (Kp), are provided to demonstrate the method of preparation and application of these elegant coatings, but they are not intended to be limiting as to amounts and the type of optional ingredients or the specific method of application of the tablet coating described herein.

EXAMPLE 1

In a Patterson-Kelley twin shell blender were placed 14.43 grams of spray-dried, coprocessed microcrystalline cellulose/iota carrageenan (70:30), 18.36 grams of polyvinylpyrrolidone 29/32 (GAF), 16.40 grams of polyethylene glycol 8000 (Union Carbide Corporation), and 0.2 grams of yellow #5 food color. After being thoroughly mixed, the dry components were added slowly to the vortex of 450 grams of deionized water being stirred in a 1 L beaker with a Lightnin' mixer. Mixing was continued for 2 hours after addition of the dry ingredients to thoroughly hydrate them. A Vector High Coater LDCS was charged with 1 Kg of 500 mg aspirin tablets, each weighing on average 0.613 gram and exhibiting friability of 0.2% after 4 minutes. The coater was operated at an inlet temperature of 100° C., an outlet temperature of 35° C., and 22 rpm with 934.5 Liters/minute (32 cubic feet/minute) of air passing through the spray coater. The previously prepared coating solution was sprayed at a pressure of 137.9 kPa (20 psi) for a period of 23 minutes. The coated tablets weighed 0.6322 gram, indicating that the coating had increased the weight of each tablet by about 3.1%. The initial hardness of these coated tablets was 7.35 Kp (average of 10 tablets). Friability of these coated tablets was 0% after 4 minutes, and disintegration time was less than 3 minutes in deionized water at 37° C. After one month of storage at room temperature, hardness was 6.55 Kp, and disintegration time was less than one minute. After two months storage at these conditions, the hardness was 6.99 Kp. Tablets stored at 40° C. and 75% relative humidity for one month had hardness of 6.67 Kp and a disintegration time of less than 5 minutes. Tablets stored for two months under these conditions had a hardness of 5.19'Kp.

EXAMPLE 2

By the method of Example 1 a dry mixture of 19.05 grams of spray-dried, coprocessed microcrystalline cellulose/iota carrageenan (70:30), 0.25 gram of hydroxyethylcellulose (Aqualon® 250 L, Hercules Incorporated), 10.40 grams of polyethylene glycol 8000, and 0.30 gram of yellow #5 food color was added to 410 grams of deionized water being stirred in a 1 L beaker with a Lightnin' mixer. After being stirred for one hour to fully hydrate the ingredients, the resulting viscous solution was sprayed using a Vector High Coater LDCS onto 1 Kg of 500 mg aspirin tablets. Conditions used include an inlet temperature of 80–85° C., an outlet temperature of 36–41° C., and 22 rpm with 1189.3 Liters/minute (42 cubic feet/minute) of air passing through the spray coater. Spraying was completed after 25 minutes. The initial thickness of these coated tablets was 6.0 mm (0.245 inch) and hardness was 7.15 Kp. Friability of the tablets was 0% after 4 minutes without any chipping or breakage. Disintegration in purified water at 37° C. was less than 2 minutes.

EXAMPLE 3

By the method of Example 1, a dry mixture of 19.05 grams of spray-dried, coprocessed microcrystalline cellulose/iota carrageenan (70:30), 0.25 gram of hydroxyethylcellulose (Aqualon® 250 L, Hercules Incorporated), 5.40 grams of polyethylene glycol 8000, 5.0 grams of Micro Talc, and 0.30 gram of red #40 food color was added to 400 grams of deionized water being stirred in a 1 L beaker with a Lightnin' mixer. After being stirred for 3 hours to fully hydrate the ingredients, the resulting viscous solution was sprayed using a Vector High Coater LDCS onto 1 Kg of 500 mg aspirin tablets, each tablet weighing on average 0.613 gram. Conditions used include an inlet temperature of 77–81° C., an outlet temperature of 39–45° C., and 23 rpm with 1047.7 Liters/minute (37 cubic feet/minute) of air passing through the spray coater. Spraying was completed after 40 minutes. The average weight of a coated tablet was 0.6334 gram, indicating that the coating had increased the weight by 3.3%. The initial thickness of these coated tablets was 6.0 mm (0.245 inch) and hardness was 8.55 Kp. Disintegration in purified water at 37° C. was less than 3 minutes. After one month of storage at room temperature, hardness was 7.61 Kp and disintegration time was less than 5 minutes. Tablets stored for two months under these conditions had a hardness of 7.99 Kp. Tablets stored at 40° C. and 75% relative humidity for one month had hardness of 7.64 Kp and a disintegration time of less than 1 minute. After two months storage the hardness was 7.34 Kp.

EXAMPLE 4

By the method of Example 1 a dry mixture of 19.05 grams of spray-dried, coprocessed microcrystalline cellulose/iota carrageenan (70:30), 0.25 gram of hydroxyethylcellulose (Aqualon® 250 L, Hercules Incorporated), 10.40 grams of polyethylene glycol 8000, and 0.30 gram of yellow #5 food color was added to 400 grams of deionized water being stirred in a 1 L beaker with a Lightnin' mixer. After being stirred for 1.5 hours to fully hydrate the ingredients, the resulting viscous solution was sprayed using a Vector High Coater LDCS onto 1 Kg of 200 mg ibuprofen tablets, each weighing 0.3114 gram. Conditions used include an inlet temperature of 73–78° C., and outlet temperature of 30–34° C., and 19–22 rpm with 1104.3 Liters/minute (39 cubic feet/minute) of air passing through the spray coater. Spraying was completed after 27 minutes. Disintegration of the uncoated tablets in purified water at 37° C. required less than 15 seconds. Friability of the uncoated tablets was 0.0677%. After being coated, the tablets weighed on average 0.3214 gram, indicating a weight gain of 3.2%. The thickness of these coated tablets was 5.99 mm (0.236 inch) and hardness was 11.47 Kp. Friability of these tablets was 0% after 4 minutes. After one month of storage at room temperature, hardness was 8.55 Kp. Tablets stored at 40° C. and 75% relative humidity for one month had hardness of 8.28 Kp. The disintegration time of tablets stored under both sets of conditions was less than 2 minutes. After two months storage at room temperature, the hardness of the coated tablets was 12.76 Kp. Storage of tablets at 40° C. and 75% relative humidity for two months increased the hardness to 13.25 Kp. Disintegration times of 30–60 seconds were recorded for tablets stored for two months under both sets of conditions.

EXAMPLE 5

By the method of Example 1 a dry mixture of 19.05 grams of spray-dried, coprocessed microcrystalline cellulose/iota carrageenan (70:30), 0.25 gram of hydroxyethylcellulose (Aqualon® 250 L, Hercules Incorporated), 10.40 grams of polyethylene glycol 8000, 0.10 gram of yellow #5 food color, and 0.10 gram of red #40 food color was added to 400 grams of deionized water being stirred in a 1 L beaker with a Lightnin' mixer. After being stirred for sufficient time to fully hydrate the ingredients, the resulting viscous solution was sprayed using a Vector High Coater LDCS onto 1 Kg of cores comprised of 20% microcrystalline cellulose and 80% calcium carbonate, each weighing on average 1.05 grams. Conditions used include an inlet temperature of 73–80° C., and outlet temperature of 36–39° C., and 19 rpm with 1104.3 Liters/minute (39 cubic feet/minute) of air passing through the spray coater. Spraying was completed in 45 minutes. The average weight of each coated tablet was 1.07 grams, indicating a weight gain of 1.9%. The thickness of these coated tablets 5.56 mm (0.219 inch) and hardness was 23.08 Kp. Friability of the tablets was 0% after 4 minutes without any chipping or breaking. Disintegration time in purified water at 37° C. was less than 3 minutes.

EXAMPLE 6

By the method of Example 1 a dry mixture of 19.05 grams of spray-dried, coprocessed microcrystalline cellulose/iota carrageenan (70:30), 10.65 grams of polyethylene glycol 8000, and 0.30 gram of yellow #5 food color was added to 400 grams of deionized water being stirred in a 1 L beaker with a Lightnin' mixer. After being stirred for some time to fully hydrate the ingredients, the resulting viscous solution was continuously stirred while it was sprayed using a Vector High Coater LDCS onto 1 Kg of the same cores of microcrystalline cellulose and calcium carbonate that were coated in Example 5. Conditions used include an inlet temperature of 78–79° C., an outlet temperature of 38–45° C., and 21–22 rpm with 1076.0 Liters/minute (38 cubic feet/minute) of air passing through the spray coater. Spraying was completed after 40 minutes. Friability of the tablets was 0% after 12 minutes without any chipping or breaking. Disintegration time in purified water at 37° C. was less than 3 minutes. This coating was not as elegant as coatings containing hydroxyethylcellulose.

EXAMPLE 7

By the method of Example 1 a dry mixture of 20.95 grams of spray-dried, coprocessed microcrystalline cellulose/iota carrageenan (70:30), 0.55 gram of hydroxyethylcellulose 250L, 11.40 grams of polyethylene glycol 8000, and 0.20 gram of yellow iron oxide was added to 450 grams of deionized water being stirred in a 1 L beaker with a Lightnin' mixer. After being stirred for about 1.5 hours to fully hydrate the ingredients, the resulting viscous solution was continuously stirred while it was sprayed using a Vector High Coater LDCS onto 1.03 Kg of compressed microcrystalline cellulose cores (Avicel® PH-200) debossed with an FMC logo, each weighing on average 0.267 gram. Conditions used include an inlet temperature of 87–90° C., an outlet temperature of 35–39° C., and 17 rpm with 1076.0 Liters/minute (38 cubic feet/minute) of air passing through the spray coater. Spraying was completed after 27 minutes. The weight of an average coated core was 0.2752 grams, indicating a coating of 3.07 weight % had been applied. Disintegration time for the uncoated cores was less than 30 seconds and for the coated cores was less than 2 minutes. Friability of the uncoated cores and the coated ones was 0% after 4 minutes without any chipping or breaking. The average thickness of the uncoated cores was 4.572 mm (0.180 inch), the thickness of the coated cores increased to 4.594 mm (0.181 inch). Uncoated cores had an average hardness of 9.14 Kp, and the hardness of the coated tablets increased to 10.35 Kp.

EXAMPLE 8

By the method of Example 1 a dry mixture of 285.75 grams of spray-dried, coprocessed microcrystalline cellulose/iota carrageenan (90:10), 7.5 grams of hydroxyethylcellulose 250L, 156.0 grams of polyethylene glycol 8000, and 45.0 grams of hydrophilic red iron oxide was prepared. A portion (60 grams) of this dry mixture was added to 540 grams of deionized water being stirred in a 1 L beaker with a Lightnin' mixer. After being stirred for a period long enough to fully hydrate the ingredients, the resulting viscous solution was continuously stirred while it was sprayed using a Vector High Coater LDCS onto about 2 Kg of acetaminophen cores. Conditions used include an inlet temperature of 73–85° C., an outlet temperature of 40–43° C., and 13 rpm with 1217.6 Liters/minute (43 cubic feet/minute) of air passing through the spray coater. Spraying was completed after 30 minutes. Coated tablets did not have as elegant an appearance as those prepared in Examples 1 through 7 in which the 70:30 combination of microcrystalline cellulose and iota carrageenan was employed. Friability testing was satisfactory, but there was minor chipping and erosion observed for these coated tablets.

EXAMPLE 9

By the method of Example 1 a dry mixture of 190.8 grams of spray-dried, coprocessed microcrystalline cellulose/iota carrageenan (70:30), 5.02 grams of hydroxyethylcellulose 250L, 104.2 grams of polyethylene glycol 8000, 1.5 grams of methyl paraben, 0.15 gram of propyl paraben, 18.48 grams of maltodextrin M-180, 4.95 grams of polysorbate 80, and 9.90 grams of Chroma Kote Red #40 was prepared. All of this dry mixture was added to 4451 grams of deionized water being stirred with a Lightnin' mixer. After being stirred for a period long enough to fully hydrate the ingredients, the resulting viscous solution was continuously stirred while it was being sprayed using an Accela Cota onto 11 Kg of Avicel® PH-200 cores containing 200 mg of chlorpheniramine maleate. Conditions used include an inlet temperature of 83–87° C., an outlet temperature of 40° C., and a 60.96 cm (24 inch) pan rotation speed of 11–12 rpm. Spraying was completed after 71 minutes. Prior to being coated the tablets had a hardness of 3.1 Kp. The coated tablets had a hardness of 3.9 and friability of 0% after 4 minutes. Disintegration of the coated tablets in 37° C. purified water required less than one minute.

EXAMPLE 10

By the method of Example 1 a dry mixture of 194.7 grams of spray-dried, coprocessed microcrystalline cellulose/iota carrageenan (70:30), 5.61 grams of hydroxyethylcellulose 250L, 106.4 grams of polyethylene glycol 8000, 1.65 grams of methyl paraben, 0.165 gram of propyl paraben, 18.48 grams of maltodextrin M-180, 4.95 grams of polysorbate 80, and 16.5 grams of Chroma Kote Red #40 was prepared. All of this dry mixture was added to 4384 grams of deionized water being stirred with a Lightnin' mixer. After being stirred for a period long enough to fully hydrate the ingredients, the resulting viscous solution was continuously stirred while it was being sprayed using an Accela Cota onto 10 Kg of multivitamin caplets. Conditions used include an inlet temperature of 75–78° C., an outlet temperature of 36–37° C., and a 60.96 cm (24 inch) pan rotation speed of 10 rpm. Spraying was completed after 95 minutes. The average weight of an uncoated caplet was 1.2503 grams. Coated caplets weighed on average 1.281 grams, indicating a coating of 2.46 weight % had been applied. Hardness of the uncoated caplets was 19.67 Kp. The hardness of the coated caplets increased to 25.14 Kp. Friability of the coated caplets after 4 minutes was 0%.

EXAMPLE 11

By the method of Example 1 a dry mixture of 68.94 grams of spray-dried, coprocessed microcrystalline cellulose/iota carrageenan (70:30), 1.82 grams of hydroxyethylcellulose 250L, 37.63 grams of polyethylene glycol 8000, 0.545 grams of methyl paraben, 0.0545 gram of propyl paraben, 10.24 grams of maltodextrin M-180, and 1.79 grams of polysorbate 80 was prepared. No coloring agent was added to this formulation. All of this dry mixture was added to 1608 grams of deionized water being stirred with a Lightnin' mixer. After being stirred for a period long enough to fully hydrate the ingredients, the resulting viscous solution was continuously stirred while it was being sprayed using an Accela Cota onto 11 Kg of round cores containing 500 mg of aspirin. Conditions used include an inlet temperature of 74–80° C., an outlet temperature of 40° C., and a 60.96 cm (24 inch) pan rotation speed of 9–11 rpm. Spraying was completed after 50 minutes. Spraying was interrupted when a coating of 0.5 weight % had been applied to the cores, and a sample weighing 1.4 Kg was removed for testing. Spraying was then resumed, and the remainder of the cores were coated to a 1.0 weight % level. The hardness of the uncoated cores was 8.25 Kp. Cores coated at 0.5 weight % had a reduced hardness of 7.5 Kp, and those coated at the 1 weight % level had a hardness of 7.87 Kp. Disintegration of cores coated at both levels was less than one minute. Prior to coating, friability of the cores after 4 minutes was greater than 6%, but at 0.5 weight % coating this was reduced to slightly greater than 1%, and, at a coating level of 1.0 weight %, it was reduced further to 0.1%.

EXAMPLE 12

In a Patterson-Kelley twin shell blender were placed 229.5 grams of a blend of microcrystalline cellulose (Avicel® PH-105, 160.65 grams) and iota carrageenan (68.85 grams), 49.5 grams of hydroxyethylcellulose (Aqualon® 250L), 148.5 grams of polyethylene glycol 8000 (Union Carbide Corporation), 13.5 grams of maltodextrin (Maltrin® M-180, Grain Processing Corporation), and 9.0 grams of yellow lake #5. After being thoroughly mixed, the dry components were added slowly to the vortex of 4550 grams of deionized water heated to 54.4° C. (130° F.) in a large beaker being stirred with a Lightnin' mixer. Mixing was continued for 2 hours after addition of the dry ingredients to thoroughly hydrate them. During hydration, the temperature of the dispersion dropped to 33.3° C. (92° F.). A Accela-Cota coater was charged with 5 Kg of 500 mg aspirin tablets, each weighing on average 0.613 gram and exhibiting friability of 0.2% after 4 minutes, and 5 Kg of ibuprofen tablets, each weighing 0.3114 gram. The coater was operated at an inlet temperature of 100–108.9° C., an outlet temperature of 40–45° C., and 10–12 rpm. During the spraying which required 53 minutes, a 3 weight percent coating, based in the weight of the tablets was applied. Upon completion of spraying, the coated tablets were allowed to dry for an additional period of 3–5 minutes before they were removed from the coater. The tablet coating had an elegant appearance. Friability was tested using 10 tablets of each type. There was no chipping or abrasion evident after 8 minutes.

EXAMPLE 13

By the method of Example 12, a dry blend comprising 238.5 grams of a blend of microcrystalline cellulose (Avicel® PH-105, 166.95 grams) and iota carrageenan (71.55 grams), 40.5 grams of hydroxyethylcellulose (Aqualon® 250L), 148.5 grams of polyethylene glycol 8000 (Union Carbide Corporation), 13.5 grams of maltodextrin (Maltrin M-180), and 9.0 grams of yellow lake #5 was dispersed in 4550 grams of deionized water heated to 45.6° C. (1 14° F.). Hydration required one hour. A Accela-Cota, coater was charged with 3.33 Kg of 500 mg aspirin tablets, each weighing on average 0.613 gram and exhibiting friability of 0.2% after 4 minutes, 3.33 Kg of acetaminophen caplets, and 3.33 Kg of ibuprofen tablets, each weighing 0.3114 gram. The coater was operated at an inlet temperature of 102.8–110.6° C., an outlet temperature of 41–47° C., and 10–12 rpm. During the spraying which required 51 minutes, a 3 weight percent coating, based in the weight of the tablets was applied. Upon completion of spraying, the coated tablets were allowed to dry for an additional period of 5 minutes before they were removed from the coater. The coating had an elegant appearance, and 10 minute friability testing of the coated aspirin and acetaminophen tablets (10 tablets of each) revealed that no chipping or damage had occurred. Disintegration times for the coated aspirin, acetaminophen, and ibuprofen tablets, was 80 seconds, 295 seconds, 26–27 minutes, respectively. The uncoated ibuprofen cores had a disintegration of about 25 minutes, however. Dissolution testing using a USP apparatus 2 (paddle) at 50 rpm, 900 mL 0.05 M phosphate buffer at 30 minutes showed that 100±0.8% of the acetaminophen had been released at pH 5.8 and 97±2.2% of the ibuprofen had been released at pH 7.2. Dissolution testing using USP apparatus 1 (basket) at 50 rpm, 500 mL 0.05 M acetate buffer, pH 4.5 showed that 93±6.9% of the aspirin had been released.

EXAMPLE 14

By the method of Example 12, a dry blend comprising 238.5 grams of a blend of microcrystalline cellulose (Avicel® PH-105, 166.95 grams) and iota carrageenan (71.55 grams), 40.5 grams of hydroxyethylcellulose (Aqualon® 250L), 148.5 grams of polyethylene glycol 8000 (Union Carbide Corporation), and 22.5 grams of maltodextrin (Maltrin M-180), was dispersed in 4550 grams of deionized water heated to 90° C. Hydration required 75 minutes. A Accela-Cota coater was charged with 12 Kg of cores comprised of 20% microcrystalline cellulose and 80% calcium carbonate, each weighing on average 1.05 grams. The coater was operated at an inlet temperature of 92.8–108.3° C., an outlet temperature of 42–46° C., and 11 rpm. During the spraying which required 76 minutes, a 3 weight percent coating, based in the weight of the tablets was applied. Upon completion of spraying, the coated tablets were allowed to dry for an additional period of 4 minutes before they were removed from the coater. The coating had an elegant appearance.

EXAMPLE 15

In a Patterson-Kelley twin shell blender were placed 234.0 grams of a blend of microcrystalline cellulose (Avicel® PH-105, 166.5 grams) and iota carrageenan (67.5 grams), 67.5 grams of hydroxyethylcellulose (Aqualon® 250L), 63.0 grams of maltodextrin (Maltrin® M-180, Grain Processing Corporation), 63.0 grams of titanium dioxide, and 22.5 grams of Red #40 aluminum lake. After being thoroughly mixed, the dry components were added slowly to the vortex of 4550 grams of deionized water at ambient temperature in a large beaker being stirred with a Lightnin' mixer. Mixing was continued until the dry ingredients were fully hydrated. A Accela-Cota coater was charged with 10 Kg of acetaminophen caplets, ibuprofen caplets, and multivitamin cores in equal amounts. The coater was operated at an inlet temperature of 102–109° C., an outlet temperature of 40–42° C., and 10 rpm. During the spraying which required 55 minutes, a 3 weight percent coating, based in the weight of the tablets, was applied. Upon completion of spraying, the coated tablets were allowed to dry for an additional period of 3–5 minutes before they were removed from the coater. The tablet coating had excellent color distribution over the tablet beads. Friability was measured using 10 tablets of each type. There was no chipping or abrasion evident after 8 minutes.

EXAMPLE 16

In a Patterson-Kelley twin shell blender were placed 76.5 grams of a blend of microcrystalline cellulose (Avicel® PH-105, 55.5 grams) and iota carrageenan (21.0 grams), 22.5 grams of hydroxyethylcellulose (Aqualon® 250L), 28.5 grams of maltodextrin (Maltrin® M-180, Grain Processing Corporation), 10.0 grams of Red #40 aluminum lake, and 0.7 gram of sodium lauryl sulfate. After being thoroughly mixed, the dry components were added slowly to the vortex of 1399.4 grams of deionized water at ambient temperature in a large beaker being stirred with a Lightnin' mixer. Mixing was continued until the ingredients were fully hydrated. A Vector High Coater LDCS was charged with 2 Kg of 500 mg acetaminophen caplets. The coater was operated at an inlet temperature of 57–70° C., an outlet temperature of 35–40° C., and 9–10 rpm. During the spraying which required 56 minutes, a 3 weight percent coating, based in the weight of the caplets, was applied. The coating was considered satisfactory, and caused no bridging of the logo, providing a good appearance of this detail.

EXAMPLE 17

In a Patterson-Kelley twin shell blender were placed 76.5 grams of a blend of microcrystalline cellulose (Avicel® PH-105, 55.5 grams) and iota carrageenan (21.0 grams), 22.5 grams of hydroxyethylcellulose (Aqualon® 250L), 28.5 grams of maltodextrin (Maltrin® M-180, Grain Processing Corporation), 10.0 grams of a red dye blend (Warner Jenkinson), and 5.0 grams of a lubricant (Eastman T L). After being thoroughly mixed, the dry components were added to 1441.0 grams of deionized water and dispersed with a Silverson mixer for 10–15 minutes. For 1.5 hours at ambient temperature the dispersion was hydrated in a large beaker while being stirred with a Lightnin' mixer. A Vector High Coater LDCS was charged with 2 Kg of 500 mg acetaminophen caplets. The coater was operated at an inlet temperature of 73–85° C., an outlet temperature of 38–44° C., and 10–11 rpm. During the spraying which required 60 minutes, a 3 weight percent coating, based in the weight of the caplets, was applied. The coating had significant sheen, did not bridge the logo, and provided complete coverage.

EXAMPLE 18

In a large Patterson-Kelley twin shell blender were placed 1.940 Kg of a blend of microcrystalline cellulose (Avicel® PH-105, 1.358 Kg) and iota carrageenan (0.582 Kg), 0.436 Kg of hydroxyethylcellulose (Aqualon® 250L), 0.277 Kg of maltodextrin (Maltrin® M-180, Grain Processing Corporation), and 1.307 Kg of polyethylene glycol 8000 (Union Carbide Corporation). After being thoroughly mixed, the dry components were added to 40.04 Kg of distilled water being stirred in a tank. For 2 hours at ambient temperature the slurry was hydrated with continued stirring. Stirring was ceased, and the coating formulation was allowed to stand for 8 hours after which it was stirred for one hour before the coating operation was commenced. A 1.22 meter (48 inch) Accela-Cota coater equipped with 4 mixing baffles was charged with 120 Kg of acetaminophen caplets containing 500 mg of active agent/caplet. The coater was operated at an inlet temperature of 62–71° C., an outlet temperature of 42–44° C., and 4–4.5 rpm. The delivery rate of coating formulation to the coater was 400 mL/minute. During the spraying which required 107 minutes, a 3 weight percent coating, based in the weight of the caplets, was applied. The coating had an elegant appearance.

Dissolution of the acetaminophen from the coated caplets was measured using USP apparatus 2 (paddle), 50 rpm, 900 mL of 0.05 M phosphate buffer at pH 5.8. Measurements of dissolved acetaminophen were made after 10, 20, and 30 minutes. Dissolution after 10 minutes was approximately 79%, 97% after 20 minutes, and 100% after 30 minutes. These dissolution rates were substantially unchanged after storing the coated tablets at 40° C., 75% humidity for up to 24 weeks, with or without desiccants.

EXAMPLE 19

In a Patterson-Kelley twin shell blender were placed 72.80 grams of a blend of microcrystalline cellulose (Avicel® PH-105, 56.25 grams) and iota carrageenan (16.55 grams), 33.08 grams of hydroxyethylcellulose (Aqualon® 250L), and 44.15 grams of hydrophilic red iron oxide. After being thoroughly mixed, the dry components were added to 1516.7 grams of deionized water and stirred for 2.5 hours at ambient temperature to fully hydrate the composition. A Vector High Coater LDCS was charged with 2 Kg of 500 mg acetaminophen caplets. The coater was operated at an inlet temperature of 81–95° C., an outlet temperature of 38–46° C., and 10 rpm. During the spraying which required 45 minutes, a 3 weight percent coating, based in the weight of the caplets, was applied. The coated tablets exhibited no friability after 8 minutes. Disintegration of the tablets required 3–4 to minutes in quiescent water at 37° C.

EXAMPLE 20

In a Patterson-Kelley twin shell blender were placed 73.5 grams of a blend of microcrystalline cellulose (Avicel® PH-105, 55.5 grams) and iota carrageenan (18.0 grams), 33.0 grams of hydroxyethylcellulose (Aqualon® 250L), 15.0 grams of maltodextrin (Maltrin® M-180, Grain Processing Corporation), and 22.5 grams of hydrophilic yellow oxide. After being thoroughly mixed, the dry components were added to 1516.7 grams of deionized water and stirred for nearly 5 hours at ambient temperature to fully hydrate the composition. A Vector High Coater LDCS was charged with 2 Kg of 500 mg acetaminophen caplets. The coater was operated at an inlet temperature of 74–83° C., an outlet temperature of 35–39° C., and 10–12 rpm. During the spraying which required 51 minutes, a 3 weight percent coating, based in the weight of the caplets, was applied. The uniformity of the color was good.

EXAMPLE 21

In a Patterson-Kelley twin shell blender were placed 73.5 grams of a blend of microcrystalline cellulose (Avicel® PH-105, 55.5 grams) and iota carrageenan (18.0 grams), 33.0 grams of hydroxyethylcellulose (Aqualon® 250L), and 21.0 grams of maltodextrin (Maltrin® M-180, Grain Processing Corporation). Simultaneously 22.5 grams of titanium dioxide was added to 1516.7 grams of deionized water and mixed for 5 minutes with a Silverson mixer. After the dry components had been thoroughly blended, they were added slowly to the vortex of the titanium dioxide dispersion which was stirred with a Lightnin' mixer for 2.25 hours at ambient temperature to fully hydrate the composition. A Vector High Coater LDCS was charged with 2 Kg of yellow multivitamin caplets weighing on average 1.258 grams. The coater was operated at an inlet temperature of 85–91° C., an outlet temperature of 38–39° C., and 11 rpm. During the spraying which required 51 minutes, a 3.5 weight percent coating, based in the weight of the caplets, was applied. The coated tablets exhibited no chipping or breakage after 10 minutes of friability testing. The yellow color was obscured completely.

EXAMPLE 22

In a Patterson-Kelley twin shell blender were placed 73.5 grams of a blend of microcrystalline cellulose (Avicel® PH-105, 55.5 grams) and iota carrageenan (18.0 grams), 33.0 grams of hydroxyethylcellulose (Aqualon® 250L), and 12.0 grams of maltodextrin (Maltrin M-180, Grain Processing Corporation). Simultaneously 31.5 grams of titanium dioxide was added to 1516.7 grams of deionized water and mixed for 5 minutes with a Silverson mixer. After the dry components had been thoroughly blended, they were added slowly to the vortex of the titanium dioxide dispersion which was stirred with a Lightnin' mixer for one hour at ambient temperature to fully hydrate the composition. A Vector High Coater LDCS was charged with 2 Kg of acetaminophen caplets that had been coated with red iron oxide. The coater was operated at an inlet temperature of 76–86° C., an outlet temperature of 33–38° C., and 13 rpm. During the spraying which required 56 minutes, a 3 weight percent coating, based in the weight of the caplets, was applied. The coated tablets exhibited no chipping or breakage after 10 minutes of friability testing. The red color of the caplets was obscured completely.

EXAMPLE 23

In a Patterson-Kelley twin shell blender were placed 78.0 grams of a blend of microcrystalline cellulose (Avicel®PH-105, 55.5 grams) and iota carrageenan (22.5 grams), 33.0 grams of hydroxyethylcellulose (Aqualon® 250L), and 9.0 grams of maltodextrin (Maltrin M-180, Grain Processing Corporation). Simultaneously 30.0 grams of titanium dioxide was added to 1516.7 grams of deionized water and mixed for 5 minutes with a Silverson mixer. After the dry components had been thoroughly blended, they were added slowly to the vortex of the titanium dioxide dispersion which was stirred at ambient temperature with a Lightnin' mixer for sufficient time to fully hydrate the composition. A Vector High Coater LDCS was charged with 2 Kg of chlorpheniramine tablets. The coater was operated at an inlet temperature of 76–80° C., an outlet temperature of 36–39° C., and 12–15 rpm. During the spraying which required 59 minutes, a 3 weight percent coating, based in the weight of the tablets, was applied. The coating covered well and obscured the color of the tablets.

EXAMPLE 24

In a Patterson-Kelley twin shell blender were placed 71.33 grams of a blend of microcrystalline cellulose (Avicel® PH-105, 49.94 grams) and iota carrageenan (21.39 grams), 16.01 grams of hydroxyethylcellulose (Aqualon® 250L), 48.05 grams of polyethylene glycol 8000 (Union Carbide Corporation), 10.19 grams of maltodextrin (Maltrin M-180, Grain Processing Corporation), and 4.5 grams of mica (White Timeron MP-10, E. M. Merck and Company). After the dry components had been thoroughly blended, they were added slowly to the vortex of 1516.7 grams deionized water which was stirred at ambient temperature with a Lightnin' mixer for sufficient time to fully hydrate the composition. A Vector High Coater LDCS was charged with 2 Kg of acetaminophen caplets. The coater was operated at an inlet temperature of 73–80° C., an outlet temperature of 35–39° C., and 8–16 rpm. During the spraying which required 57 minutes, a 3 weight percent coating, based in the weight of the caplets, was applied. The coated tablets had an elegant, opalescent appearance.

EXAMPLE 25

In a Patterson-Kelley twin shell blender were placed 78.0 grams of a blend of microcrystalline cellulose (Avicel® PH-105, 55.5 grams) and iota carrageenan (22.5 grams), 33.0 grams of hydroxyethylcellulose (Aqualon® 250L), and 1.5 gram of stearic acid. Simultaneously 37.5 grams of titanium dioxide was added to 1516.7 grams of deionized water and mixed for 5 minutes with a Silverson mixer. After the dry components had been thoroughly blended, they were added slowly to the vortex of the titanium dioxide dispersion which was stirred at ambient temperature with a Lightnin' mixer for sufficient time to fully hydrate the composition. A Vector High Coater LDCS was charged with 2 Kg of chlorpheniramine caplets. The coater was operated at an inlet temperature of 74–80° C., an outlet temperature of 33–37° C., and 13–16 rpm. During the spraying which required 54 minutes, a 3 weight percent coating, based in the weight of the caplets, was applied. This formulation coated the caplets well, and provided an elegant sheen to the coated caplets.

EXAMPLE 26

In a Patterson-Kelley twin shell blender were placed 300 grams of a blend of microcrystalline cellulose (Avicel® PH-105, 200 grams) and iota carrageenan (100 grams), and 100 grams of polyethylene glycol 8000 (Union Carbide Corporation). After the dry components had been thoroughly blended, the entire blend was added slowly to the vortex 5314.3 grams of deionized water and stirred with a Lightnin' mixer for 2.25 hours at ambient temperature to fully hydrate the composition. The suspension had a smooth appearance without any lumps. A Vector High Coater LDCS was charged with 2 Kilograms of placebo tablets. The coater was operated at an inlet temperature of 77–98° C., an outlet temperature of 32–35° C., and 12–18 rpm. During the spraying which required 187 minutes, an 15% weight percent coating, based in the weight of the tablets, was applied. The coated tablets were coated a second time using an identical formulation and coater operating conditions of an inlet temperature of 88–98° C., an outlet temperature of 40–43° C., and a pan speed of 18–19 rpm. The resulting tablets gained an increase in weight of 32%. This coating represents a possible replacement for traditional sugar coatings.

EXAMPLE 27

In a Patterson-Kelley twin shell blender were placed 49.0 grams of a blend of microcrystalline cellulose (Avicel® PH-105, 34.3 grams) and iota carrageenan (14.7 grams), 11.0 grams of hydroxyethylcellulose (Aqualon(® 250L), 33.0 grams of polyethylene glycol 8000 (Union Carbide Corporation), 7.0 grams of maltodextrin (Maltrin M-180, Grain Processing Corporation), and 1.0 grams of red dye #40 (Allied Chemical). After the dry components had been thoroughly blended, the blend was added slowly to the vortex of 1021.3 grams deionized water which was stirred with a Lightnin' mixer at ambient temperature for 2 hours to fully hydrate the composition. A Vector High Coater LDCS was charged with 2.0 Kg of yellow multivitamin caplets. The coater was operated at an inlet temperature of 65–79° C., an outlet temperature of 37–41° C., and 10–11 rpm. The coated caplets were allowed to remain in the coater for an additional minute after spraying was complete to fully dry the coating. During the spraying which required 92 minutes, a 3 weight percent coating, based in the weight of the caplets, was applied. The coated caplets had an excellent color distribution which obscured the yellow color of the caplets, and did not transfer to skin when rubbed with a finger.

EXAMPLE 28

A sample of 90 grams of the dry formulation prepared in Example 18 was dissolved in 910 mL of deionized water contained in a 2 liter glass beaker partially submerged in a circulating hot water oath at 85° C. The dry powder was added to the vortex of the water which was stirred at 1550 rpm. The addition required about one minute, and mixing was continued at 85° C. for 60 minutes. At the end of this time, a 10 mL sample of the slurry was removed and mixed 90 mL of sterile deionized water. The diluted sample was then cultured on Plate Count Agar pour plates for total aerobic bacterial measurements and on Potato Dextrose Agar with Chlortetracycline pour plates for total yeast and mold measurements. The culture plates were incubated for 5 days at 25° C. prior to enumeration. Both measurements after 48 hours were less 10 colony forming units per gram of slurry. For comparison, an identical slurry was prepared by the same method except that the temperature of the water in which the dry formulation was dispersed was 19.5° C. After incubation at 25° C., the measurements for these samples of up to 9,000 colony forming units of bacteria were observed after 24 hours, and up to 1,300 colony forming units of yeast and mold after 36 hours. This experiment shows that, provided the slurry is prepared at or above 85° C. under aseptic conditions, it is stable as an aqueous slurry for extended periods of time.

EXAMPLE 29

In a Patterson-Kelley twin shell blender were placed 43.0 grams of a blend of microcrystalline cellulose (Avicel® PH-105, 33 grams) and iota carrageenan (10 grams), 20 grams of hydroxyethylcellulose (Aqualon® 250L), 23.0 trams of triacetin, 4.0 grams of propylene glycol alginate, and 3 grams of Pluronic F-68 (BASF). After the dry components had been thoroughly blended, the blend was added slowly to the vortex o 1011.1 grams deionized water which was stirred with a Lightnin' mixer. This dispersion was stirred for 1.5 hours at ambient temperature to fully hydrate the composition. To this dispersion was added 7 grams of red #40 liquid dispersion (Crompton & Knowles). The viscosity of this dispersion was appropriate for spraying. A Vector High Coater LDCS was charged with 1 Kg of each of acetaminophen tablets and ibuprofen caplets. The coater was operated at an inlet temperature of 82–87° C., an outlet temperature of 37–42° C., and 13–15 rpm. During the spraying, which required 50 minutes, a 3 weight percent coating, based on the weight of the tablets and caplets, was applied. Friability of the tablets and caplets was 0% after 10 minutes. The resulting coating had an excellent appearance.

EXAMPLE 30

In the manner of Example 18, a coating composition was prepared by dry blending to provide a coating composition having the following formulation:

| Ingredient | Amount (g) |
| --- | --- |
| Microcrystalline cellulose (Avicel PH-105) | 37.5 |
| Iota carrageenan | 14.7 |
| Polyethylene glycol 8000 | 34 |
| Hydroxyethylcellulose 250L | 11 |
| Maltodextrin M-180 | 3 |

This formulation was dispersed in water, and the dispersion was sprayed on 2.0 Kg of acetaminophen caplets during a 49 minute period at an inlet temperature of 68–72°, an outlet temperature of 34–36°, and 9–12 rpm. A 3 weight percent coating was applied to the caplets after 10 minutes.

Dissolution of the acetaminophen from the coated caplets was measured using USP apparatus 2 (paddle), 50 rpm, 900 mL of 0.05 M phosphate buffer at pH 5.8. Measurements of dissolved acetaminophen were made after 10, 20, and 30 minutes.

The coated tablets prepared were evaluated for adhesion of the coating to the caplet in a "peel test", using a Stable Microsystems texture analyzer model TA-XT2 single column instrument with computer control and analysis. The instrument was fitted with type HDP/TCAP platens both of which were faced with double-sided foam type. The caplet was positioned centrally on the foam in the cavity of the lower platen. The upper platen was lowered and achieved a force of 800 grams on the caplet which maintained for 10 seconds after which the upper platen was withdrawn at a rate of 10 mm/sec. The data sampling rate was 500 points/sec. The maximum force required to separate the film from the tablet is defined as the "tablet coating adhesion force" and is measured in grams.

Tensile testing of the coatings was done using an Instro model 5564 single beam tester with computer control and analysis with a series IX software package. The test parameters included a gauge length of 40 mm and a crosshead speed of 2 mm/min. Films of the coatings were cast and dried at 45° C. Samples of film measuring 70 mm by 12 mm were prepared having thickness between 0.2 mm and 0.5 mm. These films were stored at 22° C. and 34% relative humidity for three days prior to testing equilibrium. The maximum percentage of elongation, the maximum stress, and Young's modulus were measured.

The results of these tests are summarized as follows:

| Dissolution (%) after | % |
| --- | --- |
| 10 minutes | 77 |
| 20 minutes | 96 |
| 30 minutes | 98 |
| Coating adhesion (grams) | 942 |
| Maximum elongation (%) | 3.34 |
| Maximum stress (mPa)[a] | 20.3 |
| Young's modulus (mPa) | 1249 |

[a]Millipascals

EXAMPLES 31 to 33

By the method of Example 19, the components of each of examples 31, 32 and 33 were dry blended to provide the formulations shown in the following table:

| | Example: | | |
| --- | --- | --- | --- |
| | 31 | 32 | 33 |
| | Weight (grams) | | |
| Avicel PH-105 | 38 | 34.3 | 34.3 |
| Iota carrageenan | 11 | 14.7 | 14.7 |
| Hydroxyethylcellulose | — | 11 | 11 |
| PGA[a] | 7 | | |
| PEG[b] | 34 | 33 | 33 |
| Lecithin[c] | 7 | 4 | 7 |
| Maltrin M-180 | 3 | 3 | |

[a]Propylene glycol alginate (Protonal ® ester SD-LB, Pronova)
[b]Polyethylene glycol 8000
[c]Hydroxylated soy lecithin The foregoing formulations were then dispersed in deionized water, the dispersion was sprayed on caplets of acetaminophen and ibuprofen, and the coated caplets were tested for friability. The dispersion and coating conditions and results of friability testing are summarized in the following table:

| | 31 | 32 | 33 |
| --- | --- | --- | --- |
| Deionized water | 1011.1 | 1011.1 | 1011.1 |
| Hydration time | 1.75 hours | 1.25 hours | >1 hour |
| Caplets | | | |
| Acetaminophen | 1 Kg | 1 Kg | 1 Kg |
| Ibuprofen | 1 Kg | 1 Kg | 1 Kg |
| Spray conditions | | | |
| Inlet temperature | 70–71° C. | 71–75° C. | 70–73° C. |
| Outlet temperature | 32–33° C. | 31–32° C. | 33–34° C. |
| Drum speed | 9–13 rpm | 10–14 rpm | 9–12 rpm |
| Time | 57 minutes | 56 minutes | >50 minutes |
| Coating weight % | 3% | 3% | 3% |
| Friability (10 minutes) | | | |
| Acetaminophen | 0% | 0% | 0% |
| Ibuprofen | 0% | 0% | 0% |

EXAMPLE 34

The dry components of this example were dry blended to provide the dry coating composition shown in the following table:

| | Weight (grams) |
| --- | --- |
| Avicel PH-105 | 33 |
| Iota carrageenan | 10 |
| Hydroxyethylcellulose | 20 |
| PGA[a] | 4 |
| Pluronic F-68 | 3 |

[a]Propylene glycol alginate (Protonal ® ester SD-LB, Pronova)

This dry formulation was dispersed in deionized water. To this dispersion were added sequentially triacetin and red #40 liquid dispersion (Crompton and Knowles). The dispersion was then sprayed on caplets, and the coated tablets were tested for friability. The dispersion, coating and testing conditions for this example is summarized in the following table:

| | |
|---|---|
| Triacetin | 23 g |
| Red #40 liquid dispersion | 7 g |
| Deionized water | 1011.1 g |
| Hydration time | 1.5 hours |
| Caplets | |
| Acetaminophen | 2 Kg |
| Spray conditions | |
| Inlet temperature | 82–87° C. |
| Outlet temperature | 37–42° C. |
| Drum speed | 13–15 rpm |
| Time | 55 minutes |
| Coating weight % | 3% |
| Friability (10 minutes) | |
| Acetaminophen | 0% |

EXAMPLE 35

By the method of Example 19, the components of this example are dry blended. The dry blend was dispersed in deionized water, then sprayed on caplets and/or tablets which were tested for friability. This example is summarized in the following table:.

| Ingredient | Weight (grams) |
|---|---|
| Avicel PH-105 | 37 |
| Iota carrageenan | 14.5 |
| Hydroxyethylcellulose | 22 |
| Mannitol[a] | 15.5 |
| Pluronic F-68 | 3 |
| Blue Lake #2 | 8 |
| Deionized water | 1150 |
| Hydration time | 2.5 |
| Caplets | |
| Ibuprofen | 1 kg |
| Acetaminophen | 1 kg |
| Spray conditions | |
| Inlet temperature | 68–74° C. |
| Outlet temperature | 30–33° C. |
| Drum speed | 12–14 rpm |
| Time | 60 minutes |
| Coating weight % | 3% |
| Friability (10 minutes) | |
| Ibuprofen | 0% |
| Chlorpheniramine | 0% |

[a]Granular mannitol

The tablets had excellent color consistency and luster. Disintegration at 37% in deionized water for acetaminophen caplets was less than 5 minutes.

The following Table 1 provides additional examples of compositions within the scope of this invention.

TABLE 1

| Example: | 36 | 37 | 38 | 39 | 40 | 41 | 42 | 43 | 44 | 45 | 46 | 47 |
|---|---|---|---|---|---|---|---|---|---|---|---|---|
| Ingredients | | | | | | | | | | | | |
| Microcrystalline cellulose | 5 | 7 | 9 | 9 | 9 | 9 | 9 | 10 | 10 | 12.3 | 13 | 15 |
| Iota Carrageenan | 15 | 15 | 14 | 14 | 14.5 | 14.5 | 15 | 10 | 14 | 14.7 | 14 | 14 |
| Polyvinylpyrrolidone | 16 | 12 | 14 | 14[a] | 14 | 10 | 14 | 14 | 14 | 10 | 5 | 5 |
| Hydroxyethylcellulose | | | | | | | | | | | | |
| Lecithin[b] | 2 | 3 | 2.5 | 3 | 2.5 | 2 | 2 | 3 | 2 | 3 | 5 | 3 |
| Lactose | 60 | 60 | 60 | 60 | 60 | 64 | 60 | 60 | 60 | 60 | 60 | 60 |
| Maltodextrin M-180 | | | | | | | | | | | | |
| Pigment/Dye (various) | 2 | 3 | | | | | | 3 | | | 3 | 3 |
| Other | | | | | | | | | | | | |
| Talc | | | | 0.5 | | 0.5 | | | | | | |
| PGA[c] | | | | | | | | | | | | |
| Dicalcium phosphate | | | | | | | | | | | | |
| Croscarmellose | | | | | | | | | | | | |
| PEG[d] | | | | | | | | | | | | |
| TOTAL | 100 | 100 | 100 | 100 | 100 | 100 | 100 | 100 | 100 | 100 | 100 | 100 |

| Example: | 48 | 49 | 50 | 51 | 52 | 53 | 54 | 55 | 56 | 57 | 58 |
|---|---|---|---|---|---|---|---|---|---|---|---|
| Ingredients | | | | | | | | | | | |
| Microcrystalline cellulose | 15 | 15 | 20 | 20 | 25 | 7 | 33 | 35 | 34.3 | 33–36 | 37.3 |
| Iota Carrageenan | 14 | 14.5 | 15 | 10 | 15 | 16 | 17 | 15 | 14.7 | 15–17 | 14.7 |
| Polyvinylpyrrolidone | 7.5 | 7.5 | | | 14 | | | | | | 11 |
| Hydroxyethylcellulose | | | 20 | 22 | 22 | | 22 | 22 | 12 | 22 | |
| Lecithin[b] | 3 | 3 | 5 | 7 | 8 | 3 | 10 | 7 | | 8–10 | |
| Lactose | 60 | 60 | 35 | | | 67 | 8 | 8 | | 9 | |
| Maltodextrin M-180 | | | | 3 | 3 | | 3 | 3 | | | 3 |
| Pigment/Dye (various) | | | 5 | 12 | 10 | | 7 | 10 | 4–5 | 10 | |

TABLE 1-continued

| Other | | | | | | | | | | | |
|---|---|---|---|---|---|---|---|---|---|---|---|
| Talc | 0.5 | | | | | | | | | | |
| PGA[c] | | | | | 7 | | 7 | | | | |
| Dicalcium phosphate | | | | | | 15 | | | | | |
| Croscarmellose | | | | | | 2 | | | | | |
| PEG[d] | | | | | | | | | | 34–35 | 34 |
| TOTAL | 100 | 100 | 100 | 100 | 100 | 100 | 100 | 100 | 100 | 100 | 100 |

[a]Kollidon ® Va-64: PVP + Acrylate
[b]Hydroxylated Soy Lecithin
[c]Profoam ®, Pronova
[d]Polyethylene glycol Comparative Example A Methyl paraben (2.0 grams) and 0.20 grams of propyl paraben were dissolved in 100 grams of propylene glycol. Upon completion of dissolution, 30.0 grams of iota carrageenan (Viscarin® SD-389, FMC Corporation) was dispersed in the propylene glycol solution. This dispersion was then added to 1800 grams of deionized water with stirring to fully hydrate the carrageenan. Microscopic examination confirmed that the carrageenan was fully hydrated. A sample of the aqueous solution was placed on a microscope slide and allowed to dry. A coherent film resulted, having both integrity and strength. However, when this aqueous solution was sprayed onto tablet cores, adhesion to the core was poor.

Comparative Example B

A dispersion of 9.30 grams of microcrystalline cellulose (Avicel® PH-102, FMC Corporation) and 20.7 grams of iota carrageenan (Viscarin® SD-389) in 1300 grams of deionized water was prepared using a Scott Turbon mixer. To this dispersion was added a solution of 0.50 gram of FD&C aluminum lake in 25 mL of ethanol. Also added to the dispersion was a solution of 0.125 gram of methyl paraben and 0.0125 gram of propyl paraben in 62 grams of propylene glycol. The entire formulation was mixed for an additional hour before being sprayed on tablet cores. Adhesion of this coating was generally poor.

While the invention has been described in detail and with reference to specific embodiments thereof, it will be apparent to one skilled in the art that various changes and modifications can be made therein without departing from the spirit and scope thereof.

We claim:

1. An edible, hardenable, prompt release pharmaceutical or veterinary solid dosage form coating composition comprising 3% to 40% microcrystalline cellulose having an average particle size less than 100 microns, a film forming amount of carrageenan, and at least one of a strengthening polymer, a plasticizer, or a surface active agent, wherein said pharmaceutical or veterinary solid dosage form coating composition does not, when ingested or placed in an aqueous medium, significantly retard release of active ingredients from a solid dosage form to which said coating is applied and said film forming amount of carrageenan is 9% to 25%.

2. The coating composition of claim 1 comprising 5% to 25% microcrystalline cellulose, 10% to 16% iota carrageenan, and 2% to 10% hydroxylated soy lecithin.

3. The coating composition of claim 2 comprising 35% to 70% lactose.

4. The coating composition of claim 3, further comprising 5% to 10% propylene glycol alginate.

5. The coating composition of claim 2 comprising 5% to 22% of hydroxyethylcellulose, or polyvinylpyrrolidone.

6. The coating composition of claim 5, further comprising 2% to 10% of a coloring agent.

7. The coating composition of claim 1 comprising 5% to 10% microcrystalline cellulose, 14% to 16% iota carrageenan, 2% to 4% hydroxylated soy lecithin, 65% to 70% lactose and 5% to 10% propylene glycol alginate.

8. The coating composition of claim 1 or 2 in which the MCC:CGN weight ratio is in the range of from about 15:85 up to 60:40.

9. The coating composition of claim 1 comprising 30% to 40% microcrystalline cellulose, 10% to 20% iota carrageenan; and 12%–25% hydroxyethylcellulose.

10. The coating composition of claim 9, further comprising 2% to 10% of a coloring agent.

11. The coating composition of claim 10, further comprising 5% to 10% hydroxylated soy lecithin and 5% to 10% lactose.

12. The coating composition of claim 10, further comprising 30% to about 35% polyethylene glycol.

13. The coating composition of claim 1, comprising 30% to 40% microcrystalline cellulose, 10% to 20% iota carrageenan, 10% to 15% polyvinylpyrrolidone, and 30% to 40% polyethylene glycol.

14. The coating composition of claim 13, further comprising from 2% to 10% coloring agent.

15. The coating composition of claim 1, wherein said strengthening polymer is at least one member selected from the group consisting of hydroxyethylcellulose, hydroxypropylcellulose, hydroxypropylmethylcellulose and polyvinylpyrrolidone.

16. The coating composition of claim 1, wherein said surface active agent is at least one member selected from the group consisting of sodium lauryl sulfate, hydroxylated soy lecithin, polysorbates, and block copolymers of propylene oxide and ethylene oxide.

17. The coating composition of claim 1, further comprising a filler selected from the group consisting of lactose and maltodextrin.

18. The coating composition of claim 1, wherein said plasticizer is at least one member selected from the group consisting of polyethylene glycol, triacetin, dibutyl sebacate, propylene glycol, sorbitol, glycerin, and triethyl citrate.

19. An edible, hardenable, prompt release pharmaceutical or veterinary coating composition comprising 3% to 40% microcrystalline cellulose, a film forming amount of carrageenan, and at least one of a strengthening polymer, a plasticizer, or a surface active agent, wherein said pharmaceutical or veterinary solid dosage form coating composition does not, when ingested or placed in an aqueous medium, significantly retard release of active ingredients from a solid dosage form to which said coating is applied and said film forming amount of carrageenan is 9% to 25%.

20. A method for coating a pharmnaceutical or veterinary solid dosage form comprising the steps of hydrating the coating composition of claim 1, followed by spray coating said hydrated coating composition onto said pharmaceutical or veterinary solid dosage form.

21. The method of claim 20, wherein said hydration time is 0.5 to 3 hours.

22. A pharmaceutical or veterinary solid dosage form coated with the coating composition of claim 1.

23. The coating composition of claim 1 further comprising a filler, wherein said filler is a carbohydrate.

24. A pharmaceutical or veterinary solid dosage form coated with the coating composition of claim 19.

25. The pharmaceutical or veterinary solid dosage form of claim 22, wherein said pharmaceutical solid dosage form is a nutraceutical solid dosage form.

26. The pharmaceutical or veterinary solid dosage form of claim 22, wherein said coating composition further comprises a carbohydrate filler.

27. The pharmaceutical or veterinary solid dosage form of claim 22, comprising 5% to 25% microcrystalline cellulose, 2% to 10% hydroxylated soy lecithin and 35% to 70% lactose.

28. The pharmaceutical or veterinary solid dosage form of claim 22, wherein said pharmaceutical or veterinary solid dosage form is a tablet.

29. The pharmaceutical or veterinary solid dosage form of claim 22, wherein said pharmaceutical or veterinary solid dosage form is a caplet.

* * * * *